United States Patent
Kwong et al.

(10) Patent No.: US 10,093,692 B2
(45) Date of Patent: Oct. 9, 2018

(54) PHOSPHINES, SYNTHESIS THEREOF AND THEIR USE IN CATALYSIS

(71) Applicant: The Hong Kong Polytechnic University, Hong Kong (CN)

(72) Inventors: Fuk Yee Kwong, Hong Kong (CN); Shun Man Wong, Hong Kong (CN); Chung Chiu Yeung, Hong Kong (CN)

(73) Assignee: The Hong Kong Polytechnic University (CN)

( * ) Notice: Subject to any disclaimer, the term of this patent is extended or adjusted under 35 U.S.C. 154(b) by 64 days.

(21) Appl. No.: 15/021,405

(22) PCT Filed: Sep. 17, 2014

(86) PCT No.: PCT/CN2014/086752
§ 371 (c)(1),
(2) Date: Mar. 11, 2016

(87) PCT Pub. No.: WO2015/039606
PCT Pub. Date: Mar. 26, 2015

(65) Prior Publication Data
US 2016/0222042 A1      Aug. 4, 2016

Related U.S. Application Data

(60) Provisional application No. 61/879,136, filed on Sep. 18, 2013.

(51) Int. Cl.
*C07F 9/6506* (2006.01)
*C07C 209/10* (2006.01)
*C07C 1/32* (2006.01)
*B01J 31/02* (2006.01)
*B01J 31/24* (2006.01)

(52) U.S. Cl.
CPC ....... *C07F 9/65068* (2013.01); *B01J 31/0271* (2013.01); *B01J 31/24* (2013.01); *C07C 1/321* (2013.01); *C07C 209/10* (2013.01); *B01J 2231/4211* (2013.01); *B01J 2231/44* (2013.01); *B01J 2531/004* (2013.01); *B01J 2531/008* (2013.01); *C07C 2531/24* (2013.01)

(58) Field of Classification Search
None
See application file for complete search history.

(56) References Cited

U.S. PATENT DOCUMENTS 6,307,087 B1   10/2001   Buchwald et al.

FOREIGN PATENT DOCUMENTS

| CN | 1791606 | 6/2006 |
|----|---------|--------|
| WO | 2002055528 A1 | 7/2002 |
| WO | 2004101581 A2 | 11/2004 |
| WO | 2009076622 A2 | 6/2009 |
| WO | 2012068335 A2 | 5/2012 |

OTHER PUBLICATIONS

Written Opinion, dated Dec. 5, 2014, for International Application No. PCT/CN2014/086752.
International Search Report, dated Dec. 5, 2014, for International Application No. PCT/CN2014/086752.
Eliana Saxon et al, 2000, "A 'Traceless' Staudinger Ligation for the Chemoselective Synthesis of Amide Bonds", Organic Letters, 2(4), 2141-2143.
Aldo Bianchi et al, 2004, "Selective synthesis of anomeric α-glycosyl acetamides via intramolecular Staudinger ligation of the α-azides", Tetrahedron Letters, 45, 2231-2234.

*Primary Examiner* — Po-Chih Chen
(74) *Attorney, Agent, or Firm* — Law Offices of Albert Wai-Kit Chan, PLLC

(57) ABSTRACT

The present invention relates to a novel class of benzimidazolyl/imidazolyl phosphine ligands, methods of preparing such ligands via a simple one-pot protocol, and applications of the ligands in catalytic reactions.

19 Claims, No Drawings

PHOSPHINES, SYNTHESIS THEREOF AND THEIR USE IN CATALYSIS

CROSS-REFERENCE TO RELATED APPLICATIONS

This application is the National Stage of International Application No. PCT/CN2014/086752, filed Sep. 17, 2014, which claims the benefit of U.S. Ser. No. 61/879,136, filed Sep. 18, 2013. The entire contents and disclosures of the preceding applications are hereby incorporated by reference into this application.

Throughout this application, various publications are referenced. Disclosures of these publications in their entireties are hereby incorporated by reference into this application in order to more fully describe the state of the art to which this invention pertains.

FIELD OF THE INVENTION

This invention relates to a novel class of phosphines, in particular, a series of benzimidazolyl/imidazolyl phosphine ligands, the synthesis thereof and their use in catalysis.

BACKGROUND OF THE INVENTION

Transition metal-catalyzed cross-coupling reactions have received significant attention, and become extremely versatile protocols in organic synthesis for the connection of carbon-carbon and/or carbon-heteroatom bonds. Particularly, various kinds of well-known coupling reactions, such as Suzuki-Miyaura reaction for the construction of diversified biaryls, Buchwald-Hartwig amination reaction for the construction of amines, Heck reaction for the construction of olefins or dienes, have numerous applications in pharmaceutical, material, and agricultural chemistry in the past few decades. The structure of ligands has been recognized as being able to significantly affect the efficiency of cross-coupling reactions. Thus, the strategic design of ligands with appropriate steric and electronic diversity, and streamlined synthetic protocol is crucial in dealing with problematic and specific substrates in this area.

The lore in this field is that the palladium catalysts contain sterically bulky and electron-rich phosphines that are effective for aromatic carbon-carbon and carbon-nitrogen bond-forming processes from aryl chlorides. Noteworthy, Beller (Zapf. A.; Sundermeier, M.; Jackstell, R.; Beller, M.; Riermeier, T; Monsees, A.; Dingerdissen, U., WO 2004/101581 A2), Buchwald (Buchwald, S. L.; Fors, B. P.; Surry, D. S., WO 2009/076622A2; Buchwald, S. L.; Old, D. W.; Wolfe, J. P.: Palucki, M.; Kamikawa, K., U.S. Pat. No. 6,307,087 B1), Fu, Hartwig and other groups highly contribute to the phosphine ligand design and synthesis.

SUMMARY OF THE INVENTION

The present invention relates to a novel class of benzimidazolyl/imidazolyl phosphine ligands which are prepared via a simple one-pot assembly from benzimidazoles/imidazoles, acid chlorides and chlorophosphines. A combination of these starting materials allows a high diversification of the ligand structure. The synthetic protocol could generate diversified entities of ligand structures via 'one-pot assembly' and 'cross-matching' approaches from three components, with several strategic points: 1) the synthetic pathway should be straightforward and streamlined; 2) the starting materials should be readily available and inexpensive; 3) the diversity and tuning of the ligand should be easily achievable; 4) the ligand synthetic steps should follow the principle of atom economy; 5) the ligand scaffold and the substituted groups should possess potential hemilabile property. Ligands are suitable for use as scaffolds in metal-ligand complexes which can serve as catalysts in further reactions. The ligands can be prepared in large scale and purified by simple re-crystallization. These ligands can exhibit exceptionally high stability in both solid and solution states.

DETAILED DESCRIPTION OF THE INVENTION

The following description of certain embodiment(s) is merely exemplary in nature and is in no way intended to limit the scope of the invention, its applications, or uses. Throughout this description, the term 'tunable' shall refer to the ability to design a chemical compound that exhibits specific properties.

The present invention relates to benzimidazolyl/imidazolyl phosphine ligands which are prepared via a simple one-pot assembly from benzimidazoles/imidazoles, acid chlorides and chlorophosphines. The present invention further includes uses of the ligands in the applications of pharmaceutical, material, and agricultural chemistry.

The ligands of the present invention are generally of the structure (1) below:

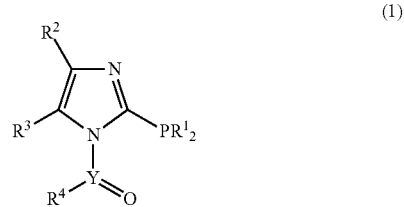

(1)

wherein Y represents C or SO;

each of the two $R^1$ independently represents alkyl; cycloalkyl, including monocyclic, bi- and tri-cyclic cycloalkyl; aryl, including phenyl, naphthyl, and fluorenyl; or heteroaryl, wherein the number of hetero atoms, selected from the group of N, O and S, may be 1 or 2; and wherein the two $R^1$ may be linked to one another;

each of $R^2$, $R^3$ and $R^4$ independently represents hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, or thiourea; wherein two or more adjacent substituents may be linked to one another to form a condensed ring system.

Additionally, in certain embodiments, the ligands of the present invention are generally of the structure (2) below:

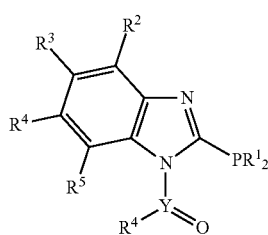

(2)

wherein Y represents C or SO;
each of the two $R^1$ groups independently represents alkyl; cycloalkyl, including monocyclic, bi- and tri-cyclic cycloalkyl; aryl, including phenyl, naphthyl, and fluorenyl; or heteroaryl, wherein the number of hetero atoms, selected from the group of N, O and S, may be 1 or 2; and wherein the two $R^1$ may be linked to one another;
each of $R^2$-$R^6$ independently represents hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, or thiourea; wherein two or more adjacent substituents may be linked to one another to form a condensed ring system.

The present invention also relates to the synthesis of the benzimidazolyl/imidazolyl phosphine by a one-pot assembly as shown in Scheme 1 below.

rhodium, iridium, ruthenium and cobalt, and the complexes can serve as catalysts in a variety of applications in pharmaceutical, material, and agricultural fields. The ligands according to the invention can generally be added in situ to appropriate transition metal precursor compounds and then used for catalytic applications.

In one embodiment, the present invention provides a phosphine ligand having the structure of formula (1):

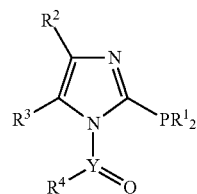

(1)

wherein Y represents C or SO:
each of the two $R^1$ independently represents alkyl; cycloalkyl, including monocyclic, bi- and tri-cyclic cycloalkyl; aryl, including phenyl, naphthyl and fluorenyl; or heteroaryl, wherein the number of hetero atoms, selected from the group of N, O and S, may be 1 or 2; and each of $R^2$, $R^3$ and $R^4$ independently represents hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epox- Scheme 1

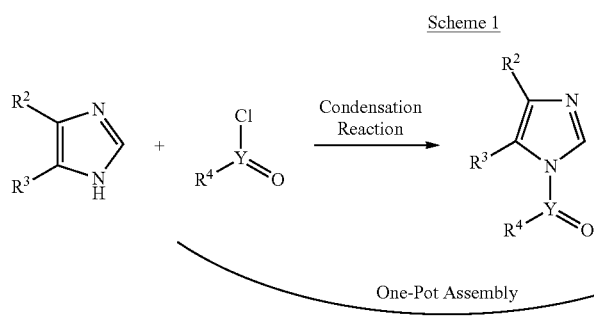

One-Pot Assembly

Scheme 1 shows the synthesis of the benzimidazolyl/imidazolyl phosphine ligands via a simple one-pot assembly from benzimidazoles/imidazoles, acid chlorides and chlorophosphines. A combination of these starting materials provides a high diversification of the ligand structure.

The starting materials are subjected to a condensation reaction in the presence of a base such as sodium hydride. The resulting intermediate is present in a yield of about 80% to 90%. The intermediate is then allowed to react with a phosphine compound. The ligand is produced in a yield of about 60% to 80% with simple purification by re-crystallization. The ligands can be prepared in a large scale. These ligands can exhibit exceptionally high stability in both solid and solution states.

The phosphine ligands synthesized by the present method are suitable for use as scaffolds in metal-ligand complexes, wherein suitable metals include nickel, palladium, platinum, ide, hydroxamic acid, imide, oxime, sulfonamide, thioamide, thiocarbamate, urea, or thiourea.

In another embodiment, the present invention provides a phosphine ligand having the structure of formula (2):

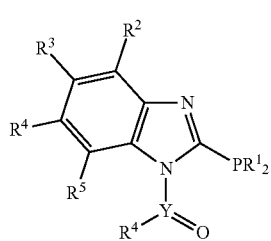

(2)

wherein Y represents C or SO;

each of the two $R^1$ groups independently represents alkyl; cycloalkyl, including monocyclic, bi- and tri-cyclic cycloalkyl; aryl, including phenyl, naphthyl and fluorenyl; or heteroaryl, wherein the number of hetero atoms, selected from the group of N, O, S, may be 1 or 2; and each of $R^2$-$R^6$ independently represents hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, or thiourea.

In one embodiment, the two $R^1$ of the phosphine ligands having the structure of formula (1) or (2) are linked to one another.

In one embodiment, two or more of $R^2$, $R^3$ and $R^4$ in the phosphine ligands having the structure of formula (1), when adjacent to one another, are linked to one another to form a condensed ring system.

In one embodiment, two or more of $R^2$, $R^3$, $R^4$, $R^5$ and $R^6$, in the phosphine ligands having the structure of formula (2), when adjacent to one another, are linked to one another to form a condensed ring system.

In one embodiment, the phosphine ligands having the structure of formula (1) or (2) is selected from the group consisting of:

2-(dicyclohexylphosphino)-N,N-diisopropyl-1H-benzo[d]imidazole-1-carboxamide (2a),
2-(di-tert-butylphosphino)-N,N-diisopropyl-1H-benzo[d]imidazole-1-carboxamide (2b),
2-(diisopropylphosphino)-N,N-diisopropyl-1H-benzo[d]imidazole-1-carboxamide (2c),
2-(diphenylphosphino)-N,N-diisopropyl-1H-benzo[d]imidazole-1-carboxamide (2d),
2-(diethylphosphino)-N,N-diisopropyl-1H-benzo[d]imidazole-1-carboxamide (2e),
2-(dicyclohexylphosphino)-N,N-diisopropyl-5,6-dimethyl-1H-benzo[d]imidazole-1-carboxamide (2i),
2-(di-tert-butylphosphino)-N,N-diisopropyl-5,6-dimethyl-1H-benzo[d]imidazole-1-carboxamide (2j),
2-(diisopropylphosphino)-N,N-diisopropyl-5,6-dimethyl-1H-benzo[d]imidazole-1-carboxamide (2k),
2-(diphenylphosphino)-N,N-diisopropyl-5,6-dimethyl-1H-benzo[d]imidazole-1-carboxamide (2l),
2-(di-o-tolylphosphino)-N,N-diisopropyl-5,6-dimethyl-1H-benzo[d]imidazole-1-carboxamide (2m),
2-(dicyclopentylphosphino)-N,N-diisopropyl-5,6-dimethyl-1H-benzo[d]imidazole-1-carboxamide (2n),
2-(dicyclohexylphosphino)-1-(2,4,6-triisopropylphenylsulfonyl)-1H-benzo[d]imidazole (2o),
2-(di-tert-butylphosphino)-1-(2,4,6-triisopropylphenylsulfonyl)-1H-benzo[d]imidazole (2p),
2-(dicyclohexylphosphino)-1-(mesitylsulfonyl)-1H-benzo[d]imidazole (2q),
2-(di-tert-butylphosphino)-1-(mesitylsulfonyl)-1H-benzo[d]imidazole (2r),
2-(di-1-adamantylphosphino)-N,N-diisopropyl-5,6-dimethyl-1H-benzo[d]imidazole-1-carboxamide (2s), and
2-(dicyclohexylphosphino)-N,N-diethyl-1H-benzo[d]imidazole-1-carboxamide (2t).

In one embodiment, the present invention further provides a method of synthesizing the phosphine ligand having the structure of formula (1), comprising the steps of: a) Condensing an appropriate imidazole with an acyl chloride or sulfonyl chloride; and b) Coupling the condensation product from step a) with an appropriate chlorophosphine to form said phosphine ligand.

In one embodiment, the present invention further provides a method of synthesizing the phosphine ligand having the structure of formula (2), comprising the steps of: a) Condensing an appropriate benzimidazole with an acyl chloride or sulfonyl chloride; and b) Coupling the condensation product from step a) with an appropriate chlorophosphine to form said phosphine ligand.

In one embodiment, step a) in the method for synthesizing the phosphine ligand having the structure of formula (1) or (2) is carried out with a base in an organic solvent. In another embodiment, the base is selected from the group consisting of sodium hydride, sodium hydroxide, potassium hydride, potassium hydroxide and calcium hydride, and the solvent is tetrahydrofuran, toluene, or a combination thereof.

In one embodiment, step b) in the method for synthesizing the phosphine ligand having the structure of formula (1) or (2) is carried out with a base. In another embodiment, the base is n-butyllithium or lithium diisopropylamide.

In one embodiment, the method for synthesizing the phosphine ligand having the structure of formula (1) or (2) is a one-pot, two-step process.

In one embodiment, the phosphine ligand having the structure of formula (1) or (2) synthesized by the methods of the present invention is selected from the group consisting of:

2-(dicyclohexylphosphino)-N,N-diisopropyl-1H-benzo[d]imidazole-1-carboxamide (2a),
2-(di-tert-butylphosphino)-N,N-diisopropyl-1H-benzo[d]imidazole-1-carboxamide (2b),
2-(diisopropylphosphino)-N,N-diisopropyl-1H-benzo[d]imidazole-1-carboxamide (2c),
2-(diphenylphosphino)-N,N-diisopropyl-1H-benzo[d]imidazole-1-carboxamide (2d),
2-(diethylphosphino)-N,N-diisopropyl-1H-benzo[d]imidazole-1-carboxamide (2e),
2-(dicyclohexylphosphino)-N,N-diisopropyl-5,6-dimethyl-1H-benzo[d]imidazole-1-carboxamide (2i),
2-(di-tert-butylphosphino)-N,N-diisopropyl-5,6-dimethyl-1H-benzo[d]imidazole-1-carboxamide (2j),
2-(diisopropylphosphino)-N,N-diisopropyl-5,6-dimethyl-1H-benzo[d]imidazole-1-carboxamide (2k),
2-(diphenylphosphino)-N,N-diisopropyl-5,6-dimethyl-1H-benzo[d]imidazole-1-carboxamide (2l),
2-(di-o-tolylphosphino)-N,N-diisopropyl-5,6-dimethyl-1H-benzo[d]imidazole-1-carboxamide (2m),
2-(dicyclopentylphosphino)-N,N-diisopropyl-5,6-dimethyl-1H-benzo[d]imidazole-1-carboxamide (2n),
2-(dicyclohexylphosphino)-1-(2,4,6-triisopropylphenylsulfonyl)-1H-benzo[d]imidazole (2o),
2-(di-tert-butylphosphino)-1-(2,4,6-triisopropylphenylsulfonyl)-1H-benzo[d]imidazole (2p),
2-(dicyclohexylphosphino)-1-(mesitylsulfonyl)-1H-benzo[d]imidazole (2q),
2-(di-tert-butylphosphino)-1-(mesitylsulfonyl)-1H-benzo[d]imidazole (2r),
2-(di-1-adamantylphosphino)-N,N-diisopropyl-5,6-dimethyl-1H-benzo[d]imidazole-1-carboxamide (2s), and
2-(dicyclohexylphosphino)-N,N-diethyl-1H-benzo[d]imidazole-1-carboxamide (2t).

In one embodiment, the method for synthesizing the phosphine ligand having the structure of formula (1) or (2) further comprises a step of purifying said phosphine ligand by recrystallization.

In one embodiment, the condensation step of ligand synthesis involves the initial activation of the N—H bond of an imidazole or benzimidazole. Most strong inorganic bases could be used in the activation. Preferably, the bases are selected from NaOH, KOH, NaH, KH and CaH. In one embodiment, a base is added to the imidazole or benzimidazole in an organic solvent at room temperature or below, preferably at −4° C. to 4° C. The organic solvent is preferably tetrahydrofuran, toluene, or a combination thereof. After the N—H bond is activated, an acyl chloride or sulfonyl chloride is added, and the mixture is then allowed to react at room temperature, but preferably under reflux condition, for 30 minutes or longer.

In one embodiment, the phosphination step of ligand synthesis involves the activation of the C-2 proton of the imidazole or benzimidazole, once the N-1 has been acylated or sulfonylated. The activation can be achieved by the use of a strong base, preferably n-butyllithium or lithium diisopropylamide (LDA), at −60° C. or below, preferably −60° C. to −98° C. The activation can be conveniently performed at −78° C. or −98° C.

In one embodiment, the present invention provides a phosphine ligand synthesized by the methods of this invention. In another embodiment, the phosphine ligand is selected from the group consisting of:
2-(dicyclohexylphosphino)-N,N-diisopropyl-1H-benzo[d]imidazole-1-carboxamide (2a),
2-(di-tert-butylphosphino)-N,N-diisopropyl-1H-benzo[d]imidazole-1-carboxamide (2b),
2-(diisopropylphosphino)-N,N-diisopropyl-1H-benzo[d]imidazole-1-carboxamide (2c),
2-(diphenylphosphino)-N,N-diisopropyl-1H-benzo[d]imidazole-1-carboxamide (2d),
2-(diethylphosphino)-N,N-diisopropyl-1H-benzo[d]imidazole-1-carboxamide (2e),
2-(dicyclohexylphosphino)-N,N-diisopropyl-5,6-dimethyl-1H-benzo[d]imidazole-1-carboxamide (2i),
2-(di-tert-butylphosphino)-N,N-diisopropyl-5,6-dimethyl-1H-benzo[d]imidazole-1-carboxamide (2j),
2-(diisopropylphosphino)-N,N-diisopropyl-5,6-dimethyl-1H-benzo[d]imidazole-1-carboxamide (2k),
2-(diphenylphosphino)-N,N-diisopropyl-5,6-dimethyl-1H-benzo[d]imidazole-1-carboxamide (2l),
2-(di-o-tolylphosphino)-N,N-diisopropyl-5,6-dimethyl-1H-benzo[d]imidazole-1-carboxamide (2m),
2-(dicyclopentylphosphino)-N,N-diisopropyl-5,6-dimethyl-1H-benzo[d]imidazole-1-carboxamide (2n),
2-(dicyclohexylphosphino)-1-(2,4,6-triisopropylphenylsulfonyl)-1H-benzo[d]imidazole (2o),
2-(di-tert-butylphosphino)-1-(2,4,6-triisopropylphenylsulfonyl)-1H-benzo[d]imidazole (2p).
2-(dicyclohexylphosphino)-1-(mesitylsulfonyl)-1H-benzo[d]imidazole (2q),
2-(di-tert-butylphosphino)-1-(mesitylsulfonyl)-1H-benzo[d]imidazole (2r).
2-(di-1-adamantylphosphino)-N,N-diisopropyl-5,6-dimethyl-1H-benzo[d]imidazole-1-carboxamide (2s), and
2-(dicyclohexylphosphino)-N,N-diethyl-1H-benzo[d]imidazole-1-carboxamide (2t).

In one embodiment, the present invention provides the use of the phosphine ligand having the structure of formula (1) or (2) to catalyze a reaction. In another embodiment, said reaction is Suzuki-Mayaura cross-coupling reaction. In a further embodiment, said reaction is Buchwald-Hartwig amination reaction.

It is to be noted that the transitional term "comprising", which is synonymous with "including", "containing" or "characterized by", is inclusive or open-ended and does not exclude additional, un-recited elements or method steps.

EXAMPLES 1 TO 28

Examples of Ligand Synthesis and Applications

EXAMPLE 1

One-pot, Two-step Synthesis of 2-(dicyclohexylphosphino)-N,N-diisopropyl-5,6-dimethyl-1H-benzo[d]imidazole-1-carboxamide (2i)

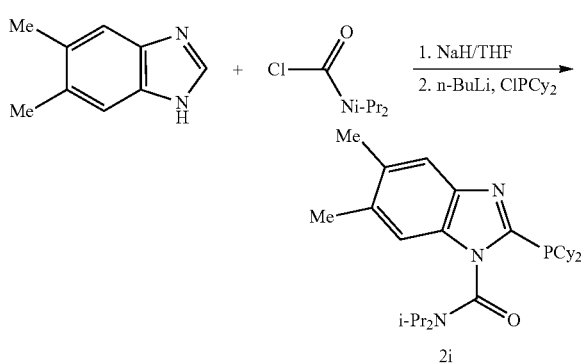

5,6-Dimethylbenzimidazole (1.46 g, 10.0 mmol) was dissolved in anhydrous THF (50 mL) and added dropwise to the THF (20 mL) solution containing 1.1 equiv of NaH (60% in mineral oil, 0.44 g, 11.0 mmol) at 0° C. (Note: NaH was pre-washed with dry hexane under nitrogen). The mixture was stirred for 20 min at room temperature. Then, 1.1 equiv of N,N-diisopropylcarbamoylchloride (1.80 g, 11.0 mmol) was added directly to the reaction and the mixture was refluxed for 30 min. After the completion of the reaction as confirmed by GC-MS analysis, solvent was removed under reduced pressure. THF (4 mL) and toluene (80 mL, the reaction mixture THF/toluene=1:20) were added. The solution was cooled to −98° C. in methanol/liquid $N_2$ bath. Titrated n-BuLi (11.0 mmol) was added dropwise by syringe. The reaction mixture was further stirred for 10 min at −98° C. and chlorodicyclohexvlphosphine (2.65 mL, 12.0 mmol) was then added dropwise by syringe. The reaction was allowed to reach room temperature and stirred for 3 h. MeOH (~10 mL) was added slowly to quench the reaction. Solvent was removed under reduced pressure. Ethyl acetate (~200 mL) and water (~100 mL) was added to the mixture and the aqueous phase was separated. The organic phase was further washed with brine (~50 mL×3), and dried by $Na_2SO_4$ and concentrated. The concentrated mixture was applied to 1×1 inch silica pad and eluted with diethyl ether. After the solvent was removed under vacuum, the white crystals (2i) (3.03 g, 65%) were obtained after re-crystallization from ether/hexane. Melting point: 162.5-165.3° C.; $^1$H NMR (400 MHz, CDCl$_3$) δ 1.26-1.95 (m, 34H), 2.39 (d, J=3.6 Hz, 6H), 3.49 (m, 2H), 7.09 (s, 1H), 7.65 (s, 1H); $^{13}$C NMR (100 MHz, CDCl$_3$) δ 19.9, 20.2, 20.4, 20.5, 20.6, 46.2, 50.6, 110.4, 120.7, 131.0, 132.2, 133.6, 139.9, 146.8, 149.2, 160.5 (complex unresolved C—P splitting was observed); $^{31}$P NMR (202 MHz, CDCl$_3$) δ −16.35; IR (cm$^{-1}$) 2970.33, 1697.80, 1634.45, 1515.61, 1438.33, 1373.10, 1331.74, 1298.93, 1234.28, 1208.02, 1157.10, 1035.95, 810.58, 626.04; MS (EI): m/z (relative intensity) 468 (M$^+$, 9), 426

(27), 386 (64), 343 (9), 304 (18), 272 (100), 259 (23), 177 (55); HRMS: calcd. for $C_{28}H_{44}N_3OPH^+$: 470.3300, found 470.3292.

EXAMPLE 2

One-pot, Two-step Synthesis of 2-(di-tert-butyl-phosphino)-N,N-diisopropyl-5,6-dimethyl-1H-benzo[d]imidazole-1-carboxamide (2j)

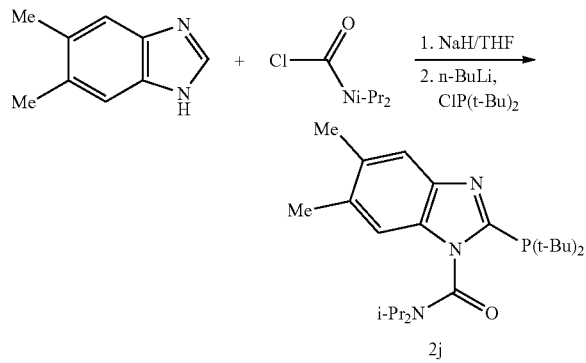

5,6-Dimethylbenzimidazole (0.73 g, 5.0 mmol) was dissolved in anhydrous THF (30 mL) and added dropwise to the THF (10 mL) solution containing 1.1 equiv of NaH (60% in mineral oil, 0.22 g, 5.5 mmol) at 0° C. (Note: NaH was pre-washed with dry hexane under nitrogen). The mixture was stirred for 20 min at room temperature. Then, 1.1 equiv of N,N-diisopropylcarbamoylchloride (0.90 g, 5.5 mmol) was added directly to the reaction and the mixture was refluxed for 30 min. After the completion of the reaction as confirmed by GC-MS analysis, the solution was cooled to −78° C. in dry ice/acetone bath. Titrated n-BuLi (6.0 mmol) was added dropwise by syringe. The reaction mixture was further stirred for 10 min at −78° C. and di-tert-butylchlorophosphine (1.14 mL, 6.0 mmol) was then added dropwise by syringe. The reaction was allowed to reach room temperature and stirred for 3 h. MeOH (~10 mL) was added slowly to quench the reaction. Solvent was removed under reduced pressure. Ethyl acetate (~100 mL) and water (~50 mL) was added to the mixture and the aqueous phase was separated. The organic phase was further washed with brine (~25 mL×3), and dried by $Na_2SO_4$ and concentrated. The concentrated mixture was applied to 1×1 inch silica pad and eluted with diethyl ether. After the solvent was removed under vacuum, the white solid (2j) (0.62 g, 30%) were obtained after re-crystallization from ether/hexane. Melting point: 179.2-181.7° C.; $^1H$ NMR (400 MHz, CDCl$_3$) δ 1.11-1.71 (m, 30H), 3.63 (m, 2H), 7.28-7.37 (m, 3H), 7.86-7.89 (m, 1H); $^{13}C$ NMR (100 MHz, CDCl$_3$) δ 20.3, 21.4, 30.3, 30.5, 33.7, 46.7, 51.1, 110.2, 120.3, 122.6, 123.6, 132.9, 133.8, 133.8, 143.9, 149.8, 153.0, 153.5 (complex unresolved C—P splitting was observed); $^{31}P$ NMR (202 MHz, CDCl$_3$) δ 14.35; IR (cm$^{-1}$) 2966.55, 1698.01, 1467.64, 1436.03, 1369.71, 1320.08, 1257.55, 1200.60, 1072.82, 1029.41, 914.88, 827.80, 748.38, 596.73, 546.15; MS (EI): m/z (relative intensity) 388 (M$^+$, 0), 346 (2), 332 (100), 276 (12), 234 (11), 205 (15), 149 (8); HRMS: calcd. for $C_{22}H_{36}N_3OPH^+$: 390.2674, found 390.2676.

EXAMPLE 3

Synthesis of N,N-diisopropyl-1H-benzo[d]imidazole-1-carboxamide (1a)

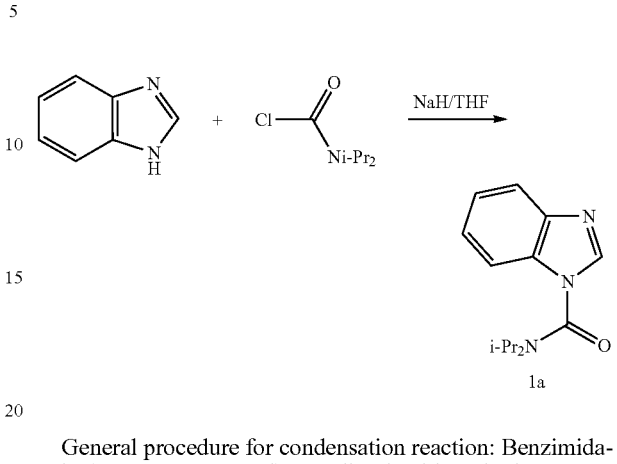

General procedure for condensation reaction: Benzimidazole (2.36 g, 20.0 mmol) was dissolved in anhydrous THF (20 mL) and added dropwise to the THF (25 mL) solution containing 1.2 equiv of NaH (60% in mineral oil, 0.96 g, 24.0 mmol) at 0° C. (Note: NaH was pre-washed with dry hexane, 5 mL×3, under nitrogen). The mixture was stirred for 30 min at room temperature. Then, 1.1 equiv of N,N-diisopropylcarbamoylchloride (3.60 g, 22 mmol) was added directly to the reaction and the mixture was refluxed for 30 min and stirred at room temperature for overnight. Solvent was removed under reduced pressure. Ethyl acetate (~300 mL) and water (~100 mL) was added to the mixture and the aqueous phase was separated. The organic phase was further washed with brine (~50 mL×3), and dried by $Na_2SO_4$ and concentrated. The concentrated mixture was applied to 2×2 inch silica pad and eluted with ethyl acetate. After the solvent was removed under vacuum, the white crystals (1a) (4.10 g, 84%) were obtained after re-crystallization from ethyl acetate/hexane. Melting point: 95.3-96.5° C.; $^1H$ NMR (400 MHz, CDCl$_3$) δ 1.44 (t, J=6.8 Hz, 12H), 3.78-3.85 (m, 2H), 7.28 (s, 1H), 7.35-7.39 (m, 1H), 7.61-7.83 (m, 1H), 7.84 (d, J=2.0 Hz, 1H), 8.06 (s, 1H); $^{13}C$ NMR (100 MHz, CDCl$_3$) δ 20.9, 49.0, 112.0, 120.3, 123.3, 124.3, 132.5, 140.3, 143.0, 149.4; IR (cm$^{-1}$) 3081.14, 3004.29, 2971.89, 2932.78, 1690.49, 1481.08, 1445.25, 1377.46, 1344.46, 1301.23, 1213.79, 1136.61, 1064.74, 1027.83, 952.93, 890.93, 829.02, 758.54, 609.88; MS (EI): m/z (relative intensity) 245 (M$^+$, 42), 145 (11), 128 (74), 118 (58), 86 (100); HRMS: calcd. for $C_{14}H_{19}N_3OH^+$: 246.1606, found 246.1610.

EXAMPLE 4

Synthesis of 2-(dicyclohexylphosphino)-N,N-diisopropyl-1H-benzo[d]imidazole-1-carboxamide (2a)

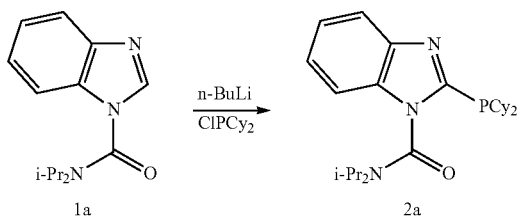

General procedure or phosphination: N,N-diisopropyl-1H-benzo[d]imidazole-1-carboxamide (1a) (1.23 g, 5.0 mmol) was dissolved in freshly distilled THF (30 mL) at room temperature under nitrogen. The solution was cooled to −78° C. in dry ice/acetone bath. Titrated n-BuLi (5.5 mmol) was added dropwise by syringe. After the reaction mixture was stirred for an hour at −78° C., chlorodicyclohexylphosphine (1.33 mL, 6.0 mmol) dissolved in 5 ml THF was added dropwise by syringe. The reaction was allowed to warm to room temperature and stirred overnight. MeOH (~10 mL) was added slowly to quench the reaction. Solvent was removed under vacuum. The crude product was applied to column chromatography and the pure product was then dried under vacuum. White solid (2a) (1.61 g, 73%) was obtained. Melting point: 205.2-206.8° C.; $^1$H NMR (400 MHz, CDCl$_3$) δ 1.11-2.70 (m, 34H), 3.39-3.60 (m, 2H), 7.29-7.36 (m, 3 H), 7.89-7.91 (m, 1H); $^{13}$C NMR (100 MHz, CDCl$_3$) δ 20.8, 26.2, 27.0, 30.0, 33.0, 34.9, 110.0, 120.0, 122.7, 123.5, 133.9, 143.7, 150.0, 153.0, 153.3 (complex unresolved C—P splitting was observed); $^{31}$P NMR (202 MHz, CDCl$_3$) δ −15.95; IR (cm$^{-1}$) 2926.88, 2848.80, 1693.42, 1437.21, 1371.58, 1329.53, 1300.93, 1255.22, 1201.02, 1147.90, 1028.78, 1002.16, 829.67, 748.43; MS (EI): m/z (relative intensity) 440 (M$^+$, 3), 398 (31), 358 (73), 276 (33), 244 (100), 231 (25), 198 (14), 149 (29); HRMS: calcd. for C$_{26}$H$_{40}$N$_3$OPH$^+$: 442.2987, found 442.3004.

EXAMPLE 5

Synthesis of 2-(di-tert-butylphosphino)-N,N-diisopropyl-1H-benzo[d]imidazole-1-carboxamide (2b)

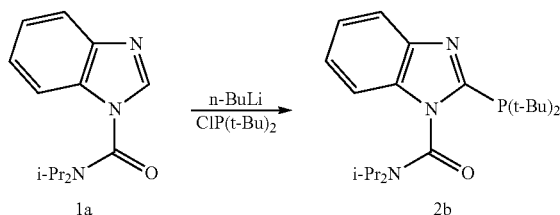

Following Example 4, N,N-diisopropyl-1H-benzo[d]imidazole-1-carboxamide (1a) (1.23 g, 5.0 mmol), titrated n-BuLi (5.5 mmol), and di-tert-butylchlorophosphine (1.14 mL, 6.0 mmol) were used to afford 2-(di-tert-butylphosphino)-N,N-diisopropyl-1H-benzo[d]imidazole-1-carboxamide (2b) (1.26 g, 65%) as white solid compound. Melting point: 179.2-181.7° C.; $^1$H NMR (400 MHz, CDCl$_3$) 1.11-1.71 (m, 30H), 3.63 (m, 2H), 7.28-7.37 (m, 3H), 7.86-7.89 (m, 1H); $^{13}$C NMR (100 MHz, CDCl$_3$) δ 20.3, 21.4, 30.3, 30.5, 33.7, 46.7, 51.1, 110.2, 120.3, 122.6, 123.6, 132.9, 133.8, 133.8, 143.9, 149.8, 153.0, 153.5 (complex unresolved C—P splitting was observed); $^{31}$P NMR (202 MHz, CDCl$_3$) δ 14.35; IR (cm$^{-1}$) 2966.55, 1698.01, 1467.64, 1436.03, 1369.71, 1320.08, 1257.55, 1200.60, 1072.82, 1029.41, 914.88, 827.80, 748.38, 596.73, 546.15; MS (EI): m/z (relative intensity) 388 (M$^+$, 0), 346 (2), 332 (100), 276 (12), 234 (11), 205 (15), 149 (8); HRMS: calcd. for C$_{22}$H$_{36}$N$_3$OPH$^+$: 390.2674, found 390.2676.

EXAMPLE 6

Synthesis of 2-(diisopropylphosphino)-N,N-diisopropyl-1H-benzo[d]imidazole-1-carboxamide (2c)

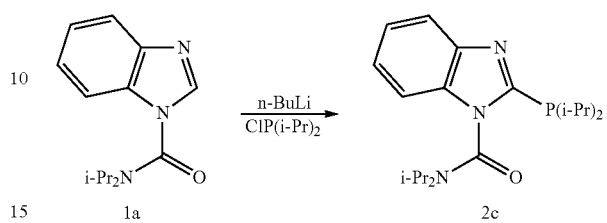

Following Example 4, N,N-diisopropyl-1H-benzo[d]imidazole-1-carboxamide (1a) (1.23 g, 5.0 mmol), titrated n-BuLi (5.5 mmol), and chlorodiisopropylphosphine (0.95 mL, 6.0 mmol) were used to afford 2-(diisopropylphosphino)-N,N-diisopropyl-1H-benzo[d]imidazole-1-carboxamide (2c) (1.21 g, 67%) as orange solid compound. Melting point: 103.4-104.7° C.; $^1$H NMR (400 MHz, CDCl$_3$) δ 1.12-1.66 (m, 26H), 2.19-2.79 (m, 2H), 3.48-3.53 (m, 2H), 7.29-7.37 (m, 3H), 7.86-7.89 (m, 1H); $^{13}$C NMR (100 MHz, CDCl$_3$) δ 19.7, 20.6, 23.1, 25.1, 110.0, 120.0, 122.7, 123.6, 133.8, 133.9, 143.6, 149.5, 153.2, 153.5 (complex unresolved C—P splitting was observed); $^{31}$P NMR (202 MHz, CDCl$_3$) δ −7.66; IR (cm$^{-1}$) 2967.35, 2869.78, 1696.43, 1456.76, 1434.64, 1373.05, 1330.37, 1304.47, 1258.39, 1206.15, 1151.88, 1032.17, 829.88, 746.24; MS (EI): m/z (relative intensity) 361 (M$^+$, 2), 318 (2), 276 (37), 244 (18), 233 (18), 191 (24), 149 (17); HRMS: calcd. for C$_{20}$H$_{32}$N$_3$OPH$^+$: 362.2361, found 362.2365.

EXAMPLE 7

Synthesis of 2-(diphenylphosphino)-N,N-diisopropyl-1H-benzo[d]imidazole-1-carboxamide (2d)

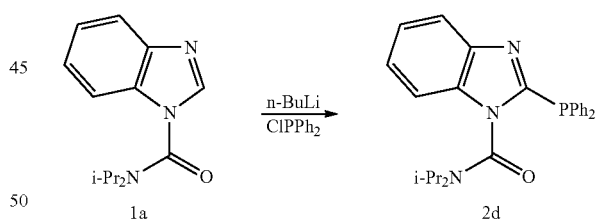

Following Example 4, N,N-diisopropyl-1H-benzo[d]imidazole-1-carboxamide (1a) (1.23 g, 5.0 mmol), titrated n-BuLi (5.5 mmol), and chlorodiphenylphosphine (1.33 mL, 6.0 mmol) were used to afford 2-(diphenylphosphino)-N,N-diisopropyl-1H-benzo[d]imidazole-1-carboxamide (2d) (1.24 g, 58%) as white solid compound. Melting point: 182.5-184.3° C.; $^1$H NMR (400 MHz, CDCl$_3$) δ 1.22-1.46 (m, 12H), 3.48-3.60 (m, 2H), 7.28-7.39 (m, 9H), 7.60-7.87 (m, 4H), 7.872 (d, J=0.8 Hz, 1H); $^{13}$C NMR (100 MHz, CDCl$_3$) δ 20.5, 49.2, 110.1, 120.7, 123.0, 124.1, 128.5, 128.6, 129.3, 133.9, 134.1, 134.2, 144.0, 149.4, 152.7, 152.8 (complex unresolved C—P splitting was observed); $^{31}$P NMR (202 MHz, CDCl$_3$) δ −25.44; IR (cm$^{-1}$) 2974.70, 1694.01, 1434.97, 1371.91, 1332.10, 1303.00, 1255.05, 1201.96, 1154.08, 1028.23, 829.83, 747.36, 693.97; MS (EI): m/z (relative intensity) 428 (M⁺, 1), 386 (14), 344 (57), 301 (25), 244 (100), 223 (20), 201 (29), 183 (45), 159 (16); HRMS: calcd. for $C_{26}H_{28}N_3OPH^+$: 430.2048, found 430.2047.

EXAMPLE 8

Synthesis of 2-(diethylphosphino)-N,N-diisopropyl-1H-benzo[d]imidazole-1-carboxamide (2e)

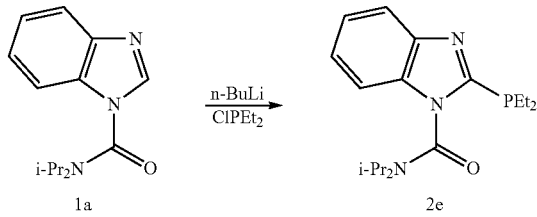

Following Example 4, N,N-diisopropyl-1H-benzo[d]imidazole-1-carboxamide (1a) (1.23 g, 5.0 mmol), titrated n-BuLi (5.5 mmol), and chlorodiethylphosphine (0.73 mL, 6.0 mmol) were used to afford 2-(diethylphosphino)-N,N-diisopropyl-1H-benzo[d]imidazole-1-carboxamide (2e) (0.86 g, 52%) as white solid compound. Melting point: 89.6-92.5° C.; ¹H NMR (400 MHz, CDCl₃) δ 1.12-1.16 (m, 6H), 1.45 (d, J=6.4 Hz, 12H), 1.88-1.98 (m, 2H), 2.12-2.19 (m, 2H), 3.52 (t, J=5.6 Hz, 2H), 7.29-7.34 (m, 3H), 7.86-7.87 (m, 1H); ¹³C NMR (100 MHz, CDCl₃) δ 9.8, 10.0, 18.4, 20.1, 20.4, 20.6, 109.8, 119.8, 120.9, 122.8, 123.6, 134.2, 143.6, 149.7, 155.1, 155.3 (complex unresolved C—P splitting was observed); ³¹P NMR (202 MHz, CDCl₃) δ −28.99; IR (cm⁻¹) 2964.92, 2931.77, 2873.92, 1692.74, 1458.29, 1430.67, 1372.97, 1329.45, 1303.45, 1261.05, 1205.70, 1154.14, 1029.23, 830.66, 744.74; MS (EI): m/z (relative intensity) 332 (M⁺, 3), 304 (45), 290 (38), 262 (15), 248 (100), 228 (23), 207 (22), 177 (28), 149 (28); HRMS: calcd. for $C_{18}H_{28}N_3OPH^+$: 334.2048, found 334.2043.

EXAMPLE 9

Synthesis of 2-(dicyclohexylphosphino)-1-methyl-1H-benzo[d]imidazole (2f)

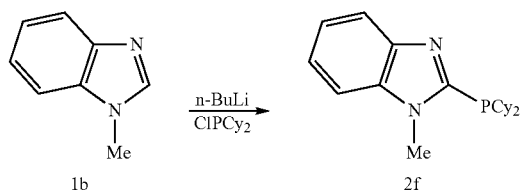

Following Example 4,1-methylbenzimidazole (1b) (0.66 g, 5.0 mmol) which is commercially available, titrated n-BuLi (5.5 mmol), and chlorodicyclohexylphosphine (1.33 mL, 6.0 mmol) were used to afford 2-(dicyclohexylphosphino)-1-methyl-1H-benzo[d]imidazole (2f) (0.98 g, 60%) as white solid compound. Melting point: 113.2-114.7° C.; ¹H NMR (400 MHz, CDCl₃) δ 1.21-1.39 (m, 10H), 1.76-1.80 (m, 8H), 1.97-1.99 (m, 2H), 2.32-2.39 (m, 2H), 3.98 (d, J=1.6 Hz, 2H), 7.30-7.41 (m, 3H), 7.87-7.91 (m, 1H); ¹³C NMR (100 MHz, CDCl₃) δ 26.2, 26.6, 26.8, 27.0, 29.2, 29.3, 30.2, 30.3, 31.1, 31.3, 33.4, 33.5, 109.4, 119.8, 121.9, 122.5, 136.3, 144.1, 154.4, 154.6 (complex unresolved C—P splitting was observed); ³¹P NMR (202 MHz, CDCl₃) δ −22.55; IR (cm⁻¹) 2921.43, 2847.08, 1443.52, 1406.85, 1318.98, 1270.75, 1235.00, 1002.19, 809.49, 758.68, 724.40; MS (EI): m/z (relative intensity) 328 (M⁺, 8), 245 (100), 213 (2), 164 (25); HRMS: calcd. for $C_{20}H_{29}N_2PH^+$: 329.2147, found 329.2133.

EXAMPLE 10

Synthesis of 2-(di-tert-butylphosphino)-1-methyl-1H-benzo[d]imidazole (2g)

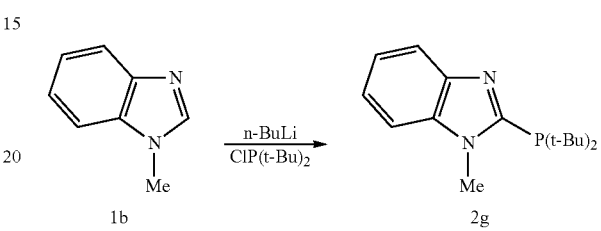

Following Example 4,1-methylbenzimidazole (1b) (0.66 g, 5.0 mmol) which is commercially available, titrated n-BuLi (5.5 mmol), and di-tert-butylchlorophosphine (1.33 mL, 6.0 mmol) were used to afford 2-(di-tert-butylphosphino)-1-methyl-1H-benzo[d]imidazole (2g) (0.51 g, 37%) as white solid compound. Melting point: 91.7-92.1° C.; ¹H NMR (400 MHz, CD₂Cl₂) δ 1.29 (s, 9H), 1.32 (s, 9H), 4.03 (s, 3H), 7.27-7.34 (m, 2H), 7.44 (d, J=7.2 Hz, 1H), 7.80 (d, J=7.2 Hz, 1H); ¹³C NMR (100 MHz, CD₂Cl₂) δ 29.7, 29.8, 31.2, 31.4, 33.1, 33.3, 109.7, 109.8, 119.7, 121.7, 122.4, 135.8, 144.0, 154.8, 155.0 (complex unresolved C—P splitting was observed); ³¹P NMR (202 MHz, CD₂Cl₂) δ 5.97; IR (cm⁻¹) 3061.02, 3046.17, 2971.12, 2939.42, 2858.50, 2361.90, 1928.69, 1893.90, 1776.58, 1672.39, 1608.70, 1591.17, 1481.15, 1467.01, 1454.30, 1430.03, 1404.22, 1384.08, 1365.23, 1351.58, 1335.71, 1314.41, 1275.81, 1232.62, 1211.35, 1176.15, 1149.73, 1137.35, 1078.10, 1027.46, 1014.59, 1004.86, 965.92, 960.42, 931.89, 896.78, 808.51, 767.34, 743.75, 726.76, 686.94, 601.94, 574.85, 555.50, 546.14, 459.20, 446.09, 416.94; MS (EI): m/z (relative intensity) 276 (M⁺, 21), 220 (62), 205 (65), 164 (100); HRMS: calcd. for $C_{16}H_{25}N_2PH^+$: 277.1834, found 227.1825.

EXAMPLE 11

Synthesis of 2-(dicyclopentylphosphino)-1-methyl-1H-benzo[d]imidazole (2h)

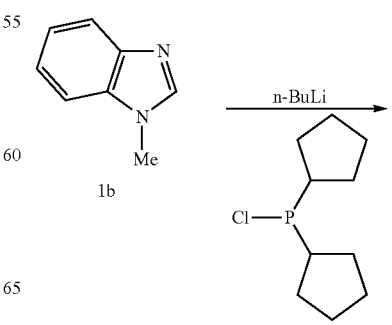

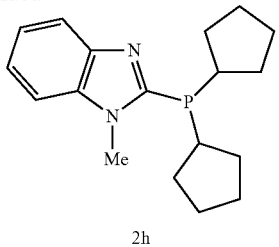

2h

Following Example 4,1-methylbenzimidazole (1b) (0.66 g, 5.0 mmol) which is commercially available, titrated n-BuLi (5.5 mmol), and chlorodicyclopentylphosphine (1.29 mL, 6.0 mmol) were used to afford 2-(dicyclopentylphosphino)-1-methyl-1H-benzo[d]imidazole (2h) (1.17 g, 65%) as white solid compound. Melting point: 74.5-78.4° C.; $^1$H NMR (400 MHz, CDCl$_3$) δ 1.26-1.29 (m, 2H), 1.48-1.73 (m, 12H), 2.02-2.06 (m, 2H), 2.63-2.66 (m, 2H), 4.01 (d, J=1.6 Hz, 3H), 7.29-7.32 (m, 2H), 7.38-7.40 (m, 1H), 7.85-7.87 (m, 1H); $^{13}$C NMR (100 MHz, CDCl$_3$) δ 25.5, 26.5, 26.6, 31.1, 37.0, 37.1, 110.0, 120.0, 122.0, 122.6, 136.1, 144.1, 156.8, 157.0 (complex unresolved C—P splitting was observed): $^{31}$P NMR (202 MHz, CDCl$_3$) δ −24.34; IR (cm$^{-1}$) 2944.91, 2857.45, 1447.26, 1406.21, 1365.01, 1314.55, 1272.97, 1233.63, 1129.77, 1084.77, 904.08, 807.87, 733.84, 681.80, 541.10, 427.17; MS (EI): m/z (relative intensity) 300 (M$^+$, 11), 231 (100), 199 (5), 164 (27); HRMS: calcd. for C$_{18}$H$_{25}$N$_2$PH$^+$: 301.1834, found 301.1826.

EXAMPLE 12

Synthesis of N,N-diisopropyl-5,6-dimethyl-1H-benzo[d]imidazole-1-carboxamide (1c)

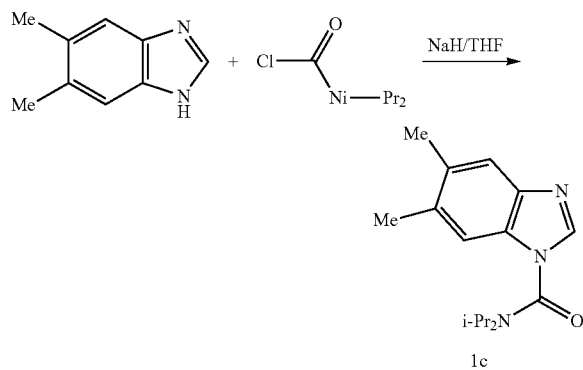

Following Example 3,5,6-Dimethylbenzimidazole (14.6 g, 100 mmol) was dissolved in anhydrous THF (230 mL) and transferred dropwise to the THF (150 mL) solution containing 1.2 equiv of NaH (60% in mineral oil, 4.8 g, 120 mmol) at 0° C. (Note: NaH was pre-washed with dry hexane, 10 mL×3, under nitrogen). The mixture was stirred for 1 h at room temperature. Then, 1.1 equiv of N,N-diisopropylcarbamoylchloride (18.0 g, 110 mmol) was added directly to the reaction and the mixture was refluxed for 1 h and stirred at room temperature for overnight. Solvent was removed under reduced pressure. Ethyl acetate (~500 mL) and water (~200 mL) was added to the mixture and the aqueous phase was separated. The organic phase was further washed with brine (~100 mL×3), and dried by Na$_2$SO$_4$ and concentrated. The concentrated mixture was applied to 2×2 inch silica pad and eluted with ethyl acetate. After the solvent was removed under vacuum, the pale yellow powder (1c) (25.2 g, 92%) was obtained after re-crystallization from ethyl acetate/hexane. Melting point: 117.1-119.5° C.; $^1$H NMR (400 MHz, CDCl$_3$) δ 1.44 (d, J=6.8 Hz, 12H), 2.41 (d, J=2.8 Hz, 6H), 3.79-3.86 (m, 2H), 7.41 (s, 1H), 7.58 (s, 1H), 7.95 (s, 1H); $^{13}$C NMR (100 MHz, CDCl$_3$) δ 20.0, 20.3, 20.8, 48.8, 112.2, 120.1, 130.9, 132.1, 133.5, 139.4, 141.5, 149.7; IR (cm$^{-1}$) 2971.93, 1681.36, 1496.99, 1433.01, 1345.52, 1304.23, 1248.68, 1211.19, 1144.93, 1097.41, 1044.36, 1019.94, 994.95, 909.64, 842.74, 754.86, 646.71, 616.50, 585.00, 554.32, 524.15, 433.79; MS (EI): m/z (relative intensity) 273 (M$^+$, 42), 173 (11), 145 (26), 128 (61), 86 (100); HRMS: calcd. for C$_{16}$H$_{23}$N$_3$OH$^+$: 274.1919, found 274.1922.

EXAMPLE 13

Synthesis of 2-(dicyclohexylphosphino)-N,N-diisopropyl-5,6-dimethyl-1H-benzo[d]imidazole-1-carboxamide (2i)

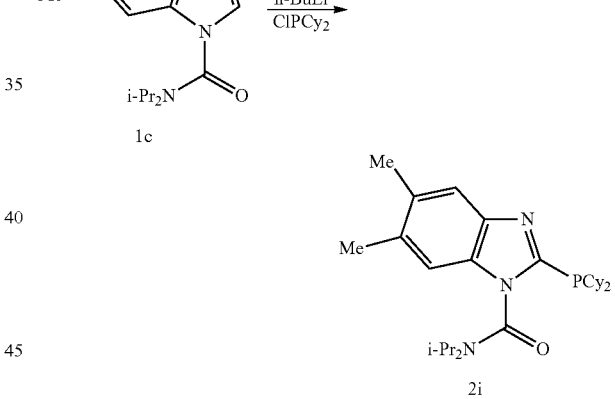

N,N-diisopropyl-5,6-dimethyl-1H-benzo[d]imidazole-1-carboxamide (1c) (1.365 g, 5.0 mmol) was dissolved in freshly distilled THF (2 mL) and toluene (40 mL, the reaction mixture THF/toluene=1:20) at room temperature under nitrogen atmosphere. The solution was cooled to −98° C. in methanol/liquid N$_2$ bath. Titrated n-BuLi (5.5 mmol) was added dropwise by syringe. The reaction mixture was further stirred for 10 min at −98° C. and chlorodicyclohexylphosphine (1.33 mL, 6.0 mmol) was then added dropwise by syringe. The reaction was allowed to reach room temperature and stirred for 3 h. MeOH (~10 mL) was added slowly to quench the reaction. Solvent was removed under reduced pressure. Ethyl acetate (~200 mL) and water (~100 mL) was added to the mixture and the aqueous phase was separated. The organic phase was further washed with brine (~50 mL×3), and dried by Na$_2$SO$_4$ and concentrated. The concentrated mixture was applied to 1×1 inch silica pad and eluted with diethyl ether. After the solvent was removed under vacuum, the white crystals (2i) (1.81 g, 77%) were obtained after re-crystallization from ether/hexane. Melting point: 162.5-165.3° C.; $^1$H NMR (400 MHz, CDCl$_3$) δ 1.26-1.95 (m, 34H), 2.39 (d, J=3.6 Hz, 6H), 3.49 (m, 2H), 7.09 (s, 1H), 7.65 (s, 1H); $^{13}$C NMR (100 MHz, CDCl$_3$) δ 19.9, 20.2, 20.4, 20.5, 20.6, 46.2, 50.6, 110.4, 120.7, 131.0, 132.2, 133.6, 139.9, 146.8, 149.2, 160.5 (complex unresolved C—P splitting was observed); $^{31}$P NMR (202 MHz, CDCl$_3$) δ −16.35; IR (cm$^{-1}$) 2970.33, 1697.80, 1634.45, 1515.61, 1438.33, 1373.10, 1331.74, 1298.93, 1234.28, 1208.02, 1157.10, 1035.95, 810.58, 626.04; MS (EI): m/z (relative intensity) 468 (M$^+$, 9), 426 (27), 386 (64), 343 (9), 304 (18), 272 (100), 259 (23), 177 (55); HRMS: calcd. for C$_{28}$H$_{44}$N$_3$OPH$^+$: 470.3300, found 470.3292.

EXAMPLE 14

Synthesis of 2-(di-tert-butylphosphino)-N,N-diisopropyl-5,6-dimethyl-1H-benzo[d]imidazole-1-carboxamide (2j)

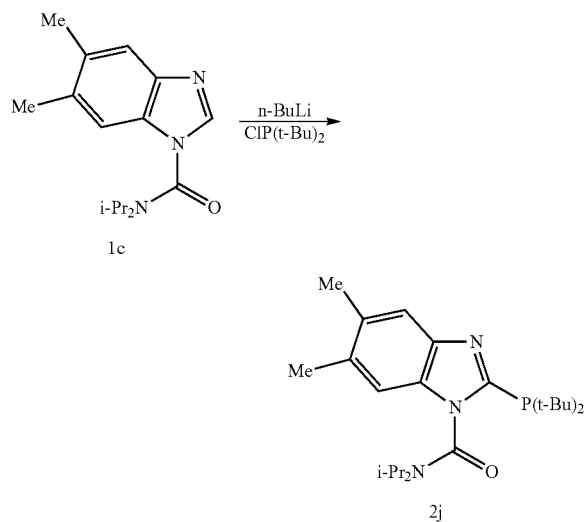

Following Example 4, N,N-diisopropyl-5,6-dimethyl-1H-benzo[d]imidazole-1-carboxamide (1c) (1.365 g, 5.0 mmol), titrated n-BuLi (5.5 mmol), and di-tert-butylchlorophosphine (1.14 mL, 6.0 mmol) were used to afford 2-(di-tert-butylphosphino)-N,N-diisopropyl-5,6-dimethyl-1H-benzo[d]imidazole-1-carboxamide (2j) (1.00 g, 48%) as white solid compound. Melting point: 168.4-171.6° C.; $^1$H NMR (400 MHz, CDCl$_3$) δ 1.14-1.68 (m, 30H), 2.63 (d, J=2.8 Hz, 6H), 3.62-3.65 (m, 2H), 7.10 (s, 1H), 7.65 (s, 1H); $^{13}$C NMR (100 MHz, CDCl$_3$) δ 20.2, 20.5, 30.3, 30.5, 33.7, 110.3, 120.2, 131.5, 132.4, 132.9, 142.6, 150.1, 151.9, 152.2 (complex unresolved C—P splitting was observed); $^{31}$P NMR (202 MHz, CDCl$_3$) δ 13.95; IR (cm$^{-1}$) 2966.65, 1696.82, 1466.79, 1436.62, 1368.95, 1311.06, 1202.72, 1169.01, 1061.29, 1026.91, 910.66, 889.34, 864.47, 837.57, 807.97, 623.78, 591.78, 527.86; MS (EI): m/z (relative intensity) 416 (M$^+$, 0), 374 (3), 360 (100), 318 (5), 304 (10), 262 (15), 233 (28), 177 (20); HRMS: calcd. for C$_{24}$H$_{40}$N$_3$OPH$^+$: 418.2987, found 418.2992.

EXAMPLE 15

Synthesis of 2-(diisopropylphosphino)-N,N-diisopropyl-5,6-dimethyl-1H-benzo[d]imidazole-1-carboxamide (2k)

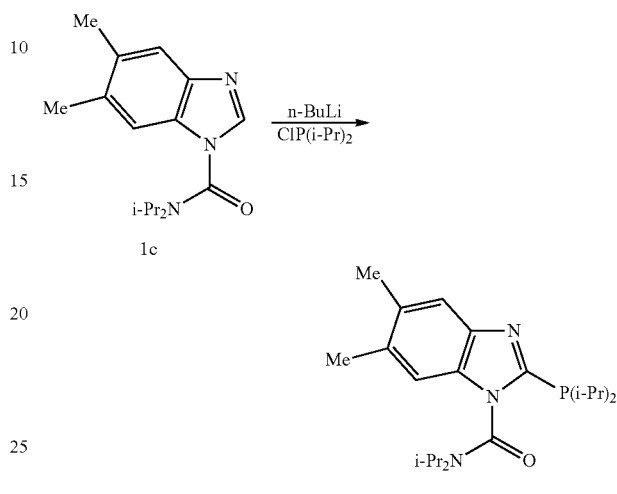

Following Example 4, N,N-diisopropyl-5,6-dimethyl-1H-benzo[d]imidazole-1-carboxamide (1c) (1.365 g, 5.0 mmol), titrated n-BuLi (5.5 mmol), and chlorodiisopropylphosphine (0.95 mL, 6.0 mmol) were used to afford 2-(diisopropylphosphino)-N,N-diisopropyl-5,6-dimethyl-1H-benzo[d]imidazole-1-carboxamide (2k) (1.11 g, 57%) as orange solid compound. Melting point: 94.8-96.4° C.; $^1$H NMR (400 MHz, CDCl$_3$) δ 1.07-1.95 (m, 26H), 2.39 (d, J=2.0 Hz, 6H), 3.51 (s, 2H), 7.10 (s, 1H), 7.63 (s, 1H); $^{13}$C NMR (100 MHz, CDCl$_3$) δ 19.7, 20.2, 20.4, 20.6, 110.1, 119.8, 131.6, 132.5, 132.9, 142.3, 149.8, 152.0, 152.3 (complex unresolved C—P splitting was observed); $^{31}$P NMR (202 MHz, CDCl$_3$) δ −8.07; IR (cm$^{-1}$) 2963.39, 2868.49, 1695.01, 1464.11, 1434.71, 1373.01, 1332.31, 1308.69, 1209.16, 1154.84, 1027.41, 1003.84, 878.00, 838.52, 619.02; MS (EI): m/z (relative intensity) 389 (M$^+$, 2), 346 (100), 304 (46), 273 (15), 262 (18), 219 (28), 177 (28), 86 (18); HRMS: calcd. for C$_{22}$H$_{36}$N$_3$OPH$^+$: 390.2674, found 390.2660.

EXAMPLE 16

Synthesis of 2-(diphenylphosphino)-N,N-diisopropyl-5,6-dimethyl-1H-benzo[d]imidazole-1-carboxamide (2l)

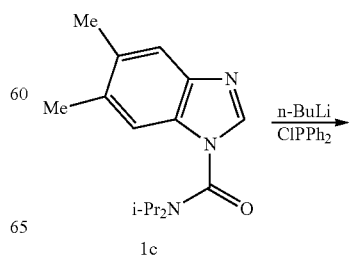

-continued

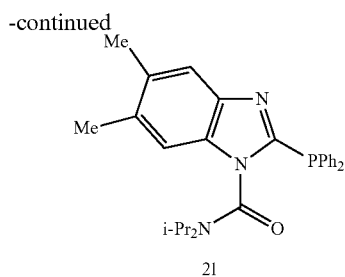
21

Following Example 4, N,N-diisopropyl-5,6-dimethyl-1H-benzo[d]imidazole-1-carboxamide (1c) (1.365 g, 5.0 mmol), titrated n-BuLi (5.5 mmol), and chlorodiphenylphosphine (0.53 mL, 2.4 mmol) were used to afford 2-(diphenylphosphino)-N,N-diisopropyl-5,6-dimethyl-1H-benzo[d]imidazole-1-carboxamide (2l) (0.38 g, 42%) as white solid compound. Melting point: 174.6-176.8° C.; $^1$H NMR (400 MHz, CDCl$_3$) δ 1.28-1.37 (m, 12H), 2.38 (d, J=5.6 Hz, 6H), 3.4-3.61 (m, 2H), 7.11-7.36 (m, 7H), 7.55-8.33 (m, 5H); $^{13}$C NMR (100 MHz, CDCl$_3$) δ 20.2, 20.5, 110.2, 120.6, 128.4, 128.5, 129.1, 132.0, 132.8, 132.9, 133.5, 133.8, 134.0, 134.5, 142.7, 149.7, 151.4, 151.5 (complex unresolved C—P splitting was observed); $^{31}$P NMR (202 MHz, CDCl$_3$) δ −25.66; IR (cm$^{-1}$) 3050.16, 2967.16, 2928.78, 1691.23, 1434.42, 1405.18, 1371.81, 1334.72, 1304.95, 1208.83, 1152.97, 1090.58, 1025.99, 883.41, 840.40, 746.11, 692.54, 623.60, 586.65, 507.68, 431.67; MS (EI): m/z (relative intensity) 456 (M$^+$, 1), 414 (15), 372 (45), 346 (9), 329 (27), 272 (100), 256 (22), 201 (25), 183 (49); HRMS: calcd. for C$_{28}$H$_{32}$N$_3$OPH$^+$: 458.2361, found 458.2369.

EXAMPLE 17

Synthesis of 2-(dio-tolylphosphino)-N,N-diisopropyl-5,6-dimethyl-1H-benzo[d]imidazole-1-carboxamide (2m)

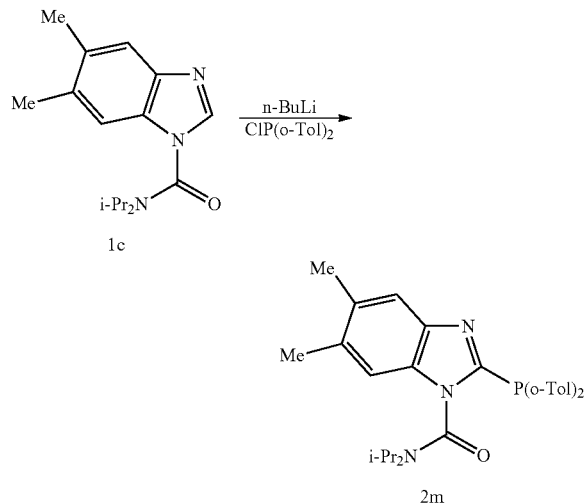

Following Example 4, N,N-diisopropyl-5,6-dimethyl-1H-benzo[d]imidazole-1-carboxamide (1c) (1.365 g, 5.0 mmol), titrated n-BuLi (5.5 mmol), and chlorodi(o-tolyl)phosphine (1.492 g, 6.0 mmol) were used to afford 2-(dio-tolylphosphino)-N,N-diisopropyl-5,6-dimethyl-1H-benzo[d]imidazole-1-carboxamide (2m) (1.60 g, 77%) as white solid compound. Melting point: 188.2-191.7° C.; $^1$H NMR (400 MHz, CDCl$_3$) δ 1.22-1.46 (m, 12H), 2.38 (d, J=6.8 Hz, 6H), 2.42 (s, 6H), 3.50-3.58 (m, 2H), 7.11-7.31 (m, 9H), 7.61 (s, 1H); $^{13}$C NMR (100 MHz, CDCl$_3$) δ 20.2, 20.5, 20.6, 21.0, 21.3, 110.2, 120.5, 125.6, 126.3, 128.5, 129.2, 130.0, 131.7, 131.9, 132.0, 133.1, 133.2, 133.3, 133.6, 135.0, 142.2, 142.4, 142.9, 149.6, 150.7, 150.8 (complex unresolved C—P splitting was observed); $^{31}$P NMR (202 MHz, CDCl$_3$) δ −39.43; IR (cm$^{-1}$) 3051.33, 2966.69, 1690.59, 14444.41, 1372.89, 1327.06, 1204.19, 1155.99, 1058.60, 835.46, 748.82, 714.18, 586.55, 447.71; MS (EI): m/z (relative intensity) 442 (M$^+$, 9), 400 (18), 357 (19), 272 (100), 229 (18), 207 (73), 187 (19), 165 (13); HRMS: calcd. for C$_{30}$H$_{36}$N$_3$OPH$^+$: 486.2674, found 486.2661.

EXAMPLE 18

Synthesis of 2-(dicydopentylphosphino)-N,N-diisopropyl-5,6-dimethyl-1H-benzo[d]imidazole-1-carboxamide (2n)

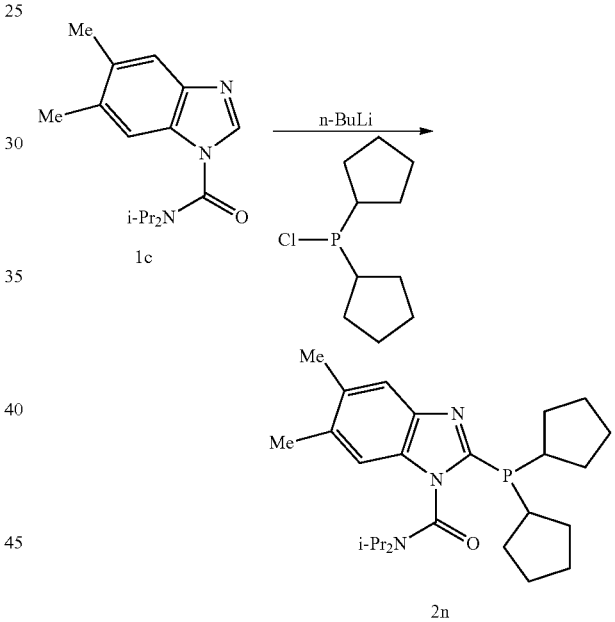

Following Example 4, N,N-diisopropyl-5,6-dimethyl-1H-benzo[d]imidazole-1-carboxamide (1c) (1.365 g, 5.0 mmol), titrated n-BuLi (5.5 mmol), and chlorodicyclopentylphosphine (1.29 mL, 6.0 mmol) were used to afford 2-(dicyclopentylphosphino)-N,N-diisopropyl-5,6-dimethyl-1H-benzo[d]imidazole-1-carboxamide (2n) (1.37 g, 62%) as white solid compound. Melting point: 171.4-172.8° C.; $^1$H NMR (400 MHz, CDCl$_3$) δ 1.27-2.44 (m, 30H), 2.54 (s, 6H), 3.54 (s, 2H), 7.10 (s, 1H), 7.61 (s, 1H); $^{13}$C NMR (100 MHz, CDCl$_3$) δ 20.2, 20.4, 25.5, 26.3, 30.5, 30.7, 110.1, 119.7, 131.6, 132.2, 132.8, 142.3, 149.7, 154.0, 154.2 (complex unresolved C—P splitting was observed); $^{31}$P NMR (202 MHz, CDCl$_3$) δ −19.70; IR (cm$^{-1}$) 2952.49, 2864.67, 1696.68, 1436.25, 1372.36, 1331.78, 1305.86, 1211.37, 1157.86, 1060.90, 1027.97, 1003.17, 894.49, 842.03, 625.66, 586.69, 523.09; MS (EI): m/z (relative intensity) 440 (M$^+$, 3), 398 (32), 358 (75), 331 (8), 315 (10), 276 (34), 259 (7), 244 (100), 228 (27); HRMS: calcd. for $C_{26}H_{40}N_3OPH^+$: 442.2987, found 442.2970.

EXAMPLE 19

Synthesis of 1-(2,4,6-triisopropylphenylsulfonyl)-1H-benzo[d]imidazole (1d)

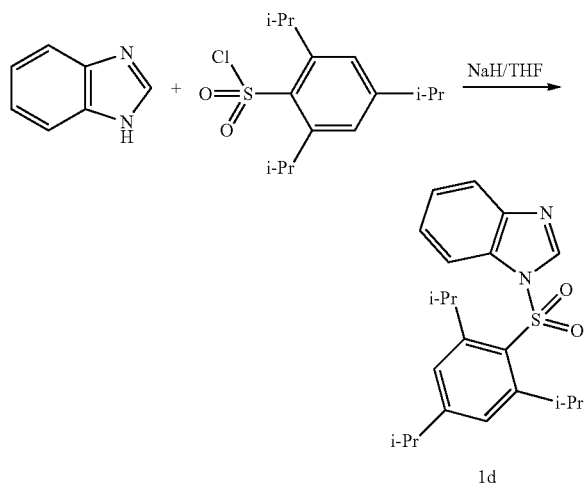

Following Example 3, Benzimidazole (2.36 g, 20.0 mmol) was dissolved in anhydrous THF (20 mL) and added dropwise to the THF (25 mL) solution containing 1.2 equiv of NaH (60% in mineral oil, 0.96 g, 24.0 mmol) at 0° C. (Note: NaH was pre-washed with dry hexane, 10 mL×3, under nitrogen). The mixture was stirred for 30 min at room temperature. Then, 1.1 equiv of 2,4,6-triisopropylbenzenesulfonyl chloride (6.66 g, 22 mmol) was added directly to the reaction and the mixture was refluxed for 30 min and stirred at room temperature for overnight. Solvent was removed under reduced pressure. Ethyl acetate (~300 mL) and water (~100 mL) was added to the mixture and the aqueous phase was separated. The organic phase was further washed with brine (~50 mL×3), and dried by $Na_2SO_4$ and concentrated. The concentrated mixture was applied to 1×1 inch silica pad and eluted with ethyl acetate. After the solvent was removed under vacuum, the white crystal (1d) (6.50 g, 85%) was obtained after re-crystallization from ethyl acetate/hexane. Melting point: 134.6-136.9° C.; $^1$H NMR (400 MHz, CDCl$_3$) δ 1.14 (d, J=6.8 Hz, 12H), 1.26 (d, J=6.8 Hz, 6H), 2.93 (septet, J=7.2 Hz, 1H), 4.18 (septet, J=6.8 Hz, 2H), 7.23 (s, 2H), 7.28-7.35 (m, 3H), 7.80 (d, J=8.0 Hz, 1H), 8.36 (s, 1H); $^{13}$C NMR (100 MHz, CDCl$_3$) δ 23.5, 24.3, 29.5, 34.2, 111.6, 120.9, 124.2, 124.5, 125.1, 130.0, 131.2, 140.5, 143.4, 151.6, 155.5; IR (cm$^{-1}$) 3447.58, 3128.15, 3057.52, 3032.29, 2967.19, 2929.17, 2870.96, 1781.20, 1611.42, 1597.78, 1555.05, 1495.68, 1475.97, 1460.62, 1447.83, 1387.03, 1371.52, 1344.48, 1306.68, 1293.92, 1258.78, 1197.09, 1182.66, 1173.06, 1159.16, 1141.02, 1104.25, 1071.32, 1061.47, 1038.33, 1022.20, 1009.98, 957.90, 939.78, 930.63, 892.40, 884.25, 844.06, 781.29, 761.95, 754.37, 743.33, 675.47; MS (EI): m/z (relative intensity) 384 (M+, 35), 305 (17), 267 (100), 251 (61), 218 (54), 203 (43), 175 (79), 159 (24), 133 (33), 118 (99), 91 (85); HRMS: calcd. for $C_{22}H_{28}N_2O_2SH^+$: 385.1950, found 385.1952.

EXAMPLE 20

Synthesis of 2-(dicyclohexylphosphino)-1-(2,4,6-triisopropylphenyl sulfonyl)-1H-benzo[d]imidazole (2o)

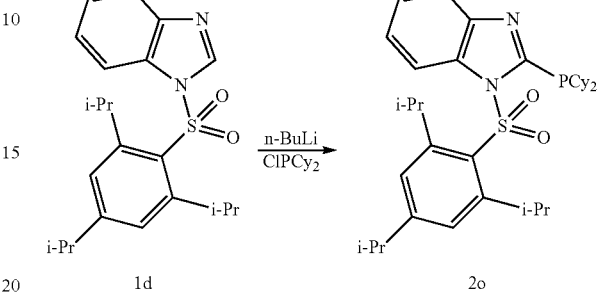

1-(2,4,6-triisopropylphenylsulfonyl)-1H-benzo[d]imidazole (1d) (1.92 g, 5.0 mmol) was dissolved in freshly distilled THF (20 mL) and toluene (40 mL, the reaction mixture THF/toluene=1:2) at room temperature under nitrogen atmosphere. The solution was cooled to –78° C. in dry ice/acetone bath. Titrated n-BuLi (5.5 mmol) was added dropwise by syringe. The reaction mixture was further stirred for 15 min at –78° C. and chlorodicyclohexylphosphine (1.33 mL, 6.0 mmol) was then added dropwise by syringe. The reaction was allowed to reach room temperature and stirred for overnight. MeOH (~10 mL) was added slowly to quench the reaction. Solvent was removed under reduced pressure. Ethyl acetate (~200 mL) and water (~100 mL) was added to the mixture and the aqueous phase was separated. The organic phase was further washed with brine (~50 mL×3), and dried by $Na_2SO_4$ and concentrated. The concentrated mixture was applied to 1×1 inch silica pad and eluted with diethyl ether. After the solvent was removed under vacuum, the white crystals (2o) (1.81 g, 77%) were obtained after re-crystallization from ether/hexane. Melting point: 208.8-210.0° C.; $^1$H NMR (400 MHz, CD$_2$Cl$_2$) δ 0.87-1.36 (m, 30H), 1.53-1.86 (m, 8H), 2.05-2.11 (m, 2H), 2.91-2.98 (m, 1H), 4.23-4.29 (m, 2H), 7.20 (s, 2H), 7.37-7.44 (m, 2H), 7.78 (d, J=7.2 Hz, 1H), 8.09 (d, J=7.6 Hz, 1H); $^{13}$C NMR (100 MHz, CD$_2$Cl$_2$) δ 26.7, 26.8, 26.9, 29.2, 29.3, 29.5, 29.6, 29.8, 34.3, 34.7, 34.8, 113.9, 120.1, 123.7, 123.8, 124.9, 133.8, 134.3, 142.8, 151.6, 155.0, 155.9, 156.3 (complex unresolved C—P splitting was observed); $^{31}$P NMR (202 MHz, CD$_2$Cl$_2$) δ –14.25; IR (cm$^{-1}$) 3447.50, 3048.54, 2927.62, 2850.75, 1599.22, 1583.18, 1560.10, 1550.26, 1459.10, 1445.69, 1426.76, 1375.85, 1346.95, 1332.42, 1292.71, 1251.55, 1229.16, 1181.46, 1157.48, 1142.31, 1106.33, 1057.58, 1037.79, 1023.23, 1011.10, 938.35, 902.43, 881.00, 850.61, 844.69, 816.68, 765.34, 746.69, 671.77, 654.25, 646.00, 624.02, 607.44, 575.97, 557.33, 542.45, 523.35, 433.64, 418.76; MS (EI): m/z (relative intensity) 580 (M+, 0), 383 (100), 231 (23), 207 (19); HRMS: calcd. for $C_{34}H_{49}N_2O_2SPH^+$: 581.3331, found 581.3306.

EXAMPLE 21

Synthesis of 2-(di-tert-butylphosphino)-1-(2,4,6-triisopropylphenyl sulfonyl)-1H-benzo[d]imidazole (2p)

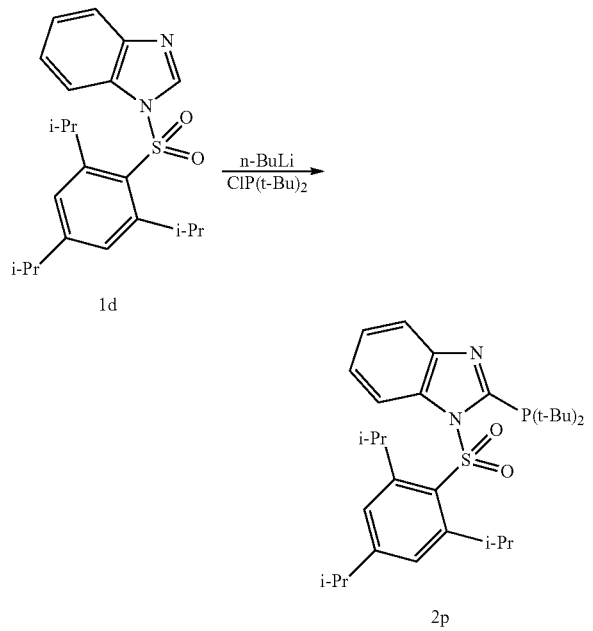

1-(2,4,6-triisopropylphenylsulfonyl)-1H-benzo[d]imidazole (1d) (1.15 g, 3.0 mmol) was dissolved in freshly distilled THF (20 mL) at room temperature under nitrogen atmosphere. The solution was cooled to −78° C. in dry ice/acetone bath. Titrated n-BuLi (3.3 mmol) was added dropwise by syringe. The reaction mixture was further stirred for 15 min at −78° C. and di-tert-butylchlorophosphine (0.68 mL, 3.6 mmol) was then added dropwise by syringe. The reaction was allowed to reach room temperature and stirred for overnight. MeOH (~10 mL) was added slowly to quench the reaction. Solvent was removed under reduced pressure. Ethyl acetate (~200 mL) and water (~100 mL) was added to the mixture and the aqueous phase was separated. The organic phase was further washed with brine (~50 mL×3), and dried by $Na_2SO_4$ and concentrated. The concentrated mixture was applied to 1×1 inch silica pad and eluted with diethyl ether. After the solvent was removed under vacuum, the orange solid (2p) (0.46 g, 29%) were obtained after re-crystallization from etherhexane. Melting point: 165.6-166.2° C.; $^1$H NMR (400 MHz, $CD_2Cl_2$) δ 1.04-1.09 (m, 30H), 1.24-1.29 (m, 8H), 2.88-2.98 (m, 1H), 4.35 (s, 2H), 7.20 (s, 2H), 7.40 (t, J=7.6 Hz, 1H), 7.46 (t, J=7.2 Hz, 1H), 7.81 (d, J=8.0 Hz, 1H), 8.24 (d, J=8.0 Hz, 1H); $^{13}$C NMR (100 MHz, $CD_2Cl_2$) δ 23.2, 23.8, 24.4, 29.2, 29.3, 29.8, 29.9, 33.8, 34.0, 34.4, 114.4, 120.4, 123.6, 123.8, 125.2, 133.9, 134.2, 142.5, 151.9, 152.0, 154.8, 155.0, 155.2 (complex unresolved C—P splitting was observed); $^{31}$P NMR (202 MHz, $CD_2Cl_2$) δ 10.48; IR (cm$^{-1}$) 3287.51, 3053.72, 2966.91, 2894.06, 2865.47, 2361.74, 1601.34, 1566.93, 1460.26, 1430.30, 1374.55, 1346.83, 1331.45, 1251.48, 1225.27, 1177.87, 1130.04, 1107.20, 1070.78, 1057.94, 1035.59, 1012.81, 940.62, 903.40, 885.54, 846.26, 816.00, 762.51, 753.64, 742.24, 670.41, 627.58, 609.64, 576.50, 556.12, 547.25, 522.55, 459.86, 435.54, 434.83, 425.33; MS (EI): m/z (relative intensity) 528 (M$^+$, 13), 471 (6), 415 (7), 383 (16), 367 (34), 351 (31), 309 (21), 262 (37), 233 (12), 205 (33), 175 (20), 150 (100), 119 (24), 91 (27), 57 (56); HRMS: calcd. for $C_{30}H_{45}N_2O_2SPH^+$: 529.3018, found 529.3035.

EXAMPLE 22

Synthesis of 1-(mesitylsulfonyl)-1H-benzo[d]imidazole (1e)

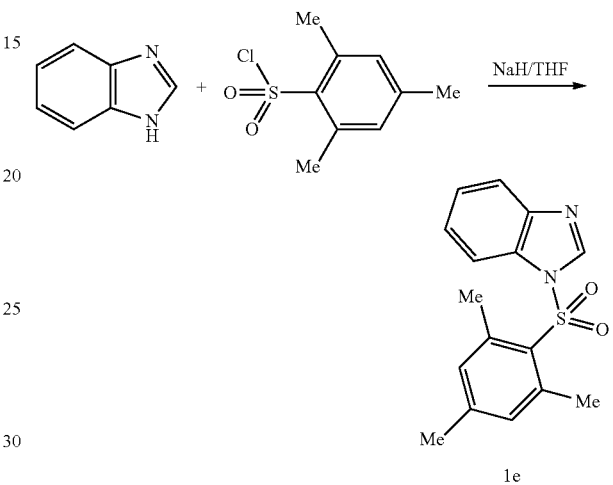

Following Example 3, Benzimidazole (2.36 g, 20.0 mmol) was dissolved in anhydrous THF (20 mL) and added dropwise to the THF (25 mL) solution containing 1.2 equiv of NaH (60% in mineral oil, 0.96 g, 24.0 mmol) at 0° C. (Note: NaH was pre-washed with dry hexane, 10 mL×3, under nitrogen). The mixture was stirred for 30 min at room temperature. Then, 1.1 equiv of 2-mesitylenesulfonyl chloride (4.81 g, 22 mmol) was added directly to the reaction and the mixture was refluxed for 30 h and stirred at room temperature for overnight. Solvent was removed under reduced pressure. Ethyl acetate (~300 mL) and water (~100 mL) was added to the mixture and the aqueous phase was separated. The organic phase was further washed with brine (~50 mL×3), and dried by $Na_2SO_4$ and concentrated. The concentrated mixture was applied to 1×1 inch silica pad and eluted with ethyl acetate. After the solvent was removed under vacuum, the white crystal (1e) (3.69 g, 62%) was obtained after re-crystallization from ethyl acetate/hexane. Melting point: 113.7-115.8° C.; $^1$H NMR (400 MHz, $CDCl_3$) δ 2.32 (s, 3H), 2.60 (s, 1H), 7.01 (s, 2H), 7.27-7.36 (m, 3H), 7.81 (d, J=8.0 Hz, 1H), 8.45 (s, 1H); $^{13}$C NMR (100 MHz, $CDCl_3$) δ 21.0, 22.5, 111.6, 121.0, 124.3, 125.2, 130.8, 131.3, 132.6, 140.4, 141.4, 143.7, 145.1; IR (cm$^{-1}$) 3447.21, 3125.47, 2980.62, 1772.53, 1700.33, 1684.45, 1653.26, 1635.63, 1616.87, 1601.46, 1576.53, 1559.09, 1539.82, 1521.46, 1516.93, 1506.62, 1496.31, 1472.33, 1445.56, 1419.45, 1401.03, 1387.17, 1352.33, 1309.51, 1288.61, 1253.98, 1190.14, 1165.72, 1127.65, 1056.36, 1033.40, 1021.04, 939.68, 893.10, 882.96, 857.45, 779.42, 765.57, 749.40, 711.67, 677.48, 650.43, 616.39, 590.90, 580.23, 526.97, 486.01, 418.71; MS (EI): m/z (relative intensity) 300 (M$^+$, 28), 235 (7), 183 (9), 119(100), 103 (7), 91 (24), 77 (11), 63 (7); HRMS: calcd. for $C_{16}H_{16}N_2O_2SH^+$: 301.1011, found 301.0998.

EXAMPLE 23

Synthesis of 2-(dicyclohexylphosphino)-1-(mesitylsulfonyl)-1H-benzo[d]imidazole (2q)

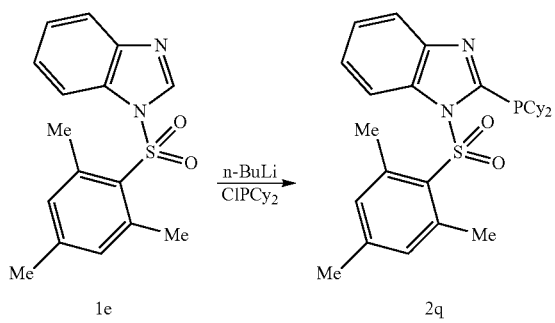

1-(mesitylsulfonyl)-1H-benzo[d]imidazole (1e) (1.50 g, 5.0 mmol) was dissolved in freshly distilled THF (20 mL) and toluene (40 mL, the reaction mixture THF/toluene=1:2) at room temperature under nitrogen atmosphere. The solution was cooled to −78° C. in dry ice/acetone bath. Titrated n-BuLi (5.5 mmol) was added dropwise by syringe. The reaction mixture was further stirred for 15 min at −78° C. and chlorodicyclohexylphosphine (1.33 mL, 6.0 mmol) was then added dropwise by syringe. The reaction was allowed to reach room temperature and stirred for overnight. MeOH (~10 mL) was added slowly to quench the reaction. Solvent was removed under reduced pressure. Ethyl acetate (~200 mL) and water (~100 mL) was added to the mixture and the aqueous phase was separated. The organic phase was further washed with brine (~50 mL×3), and dried by $Na_2SO_4$ and concentrated. The concentrated mixture was applied to 1×1 inch silica pad and eluted with diethyl ether. After the solvent was removed under vacuum, the white crystals (2q) (1.47 g, 60%) were obtained after re-crystallization from ether/hexane. Melting point: 169.1-170.8° C.; $^1$H NMR (400 MHz, $CD_2Cl_2$) δ 0.89-1.35 (m, 12H), 1.55-1.81 (m, 8H), 2.05-2.11 (m, 2H), 2.34 (s, 3H), 2.47 (s, 6H), 6.99 (s, 2H), 7.37-7.44 (m, 2H), 7.79 (d, J=6.4 Hz, 1H), 8.12 (d, J=7.2 Hz, 1H); $^{13}$C NMR (100 MHz, $CD_2Cl_2$) δ 22.6, 26.2, 26.7, 26.8, 26.9, 29.4, 29.5, 29.7, 29.9, 34.8, 34.9, 114.7, 120.2, 123.8, 125.0, 131.8, 134.9, 135.3, 140.62, 140.64, 142.7, 144.5, 156.1, 156.5 (complex unresolved C—P splitting was observed); $^{31}$P NMR (202 MHz, $CD_2Cl_2$) δ −13.58; IR ($cm^{-1}$) 3447.52, 2917.15, 2849.51, 1601.72, 1583.65, 1559.98, 1458.06, 1444.02, 1428.95, 1405.36, 1360.72, 1331.76, 1292.23, 1254.65, 1230.73, 1179.17, 1168.51, 1157.34, 1135.47, 1105.03, 1053.46, 1027.42, 1011.52, 903.46, 884.92, 850.87, 817.37, 768.05, 747.20, 718.29, 670.25, 643.83, 607.84, 587.04, 573.60, 562.09, 549.52, 532.72, 525.85, 510.92; MS (EI): m/z (relative intensity) 496 ($M^+$, 0), 349 (15), 299 (100), 267 (9), 207 (30), 149 (14), 117 (12); HRMS: calcd. for $C_{28}H_{37}N_2O_2SPH^+$: 497.2392, found 497.2375.

EXAMPLE 24

Synthesis of 2-(di-tert-butylphosphino)-1-(mesitylsulfonyl)-1H-benzo[d]imidazole (2r)

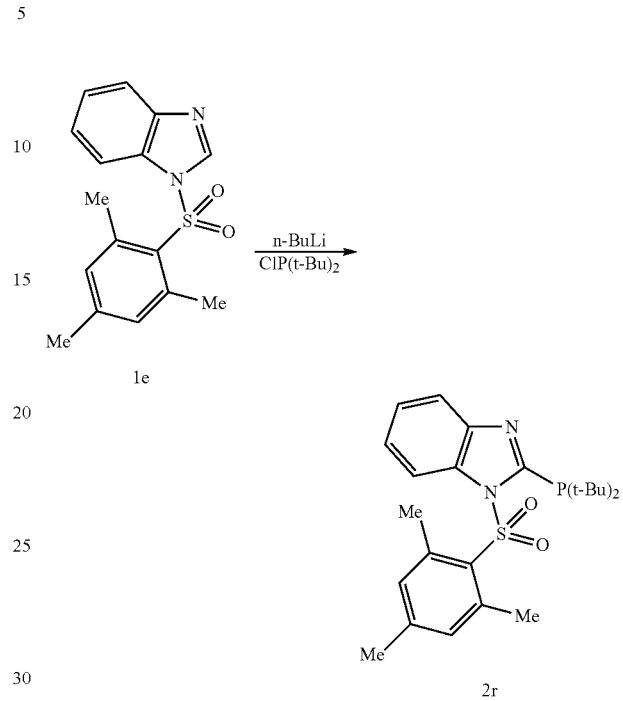

1-(mesitylsulfonyl)-1H-benzo[d]imidazole (1e) (0.90 g, 3.0 mmol) was dissolved in freshly distilled THF (20 mL) at room temperature under nitrogen atmosphere. The solution was cooled to −78° C. in dry ice/acetone bath. Titrated n-BuLi (3.3 mmol) was added dropwise by syringe. The reaction mixture was further stirred for 15 min at −78° C. and di-tert-butylchlorophosphine (0.68 mL, 3.6 mmol) was then added dropwise by syringe. The reaction was allowed to reach room temperature and stirred for overnight. MeOH (~10 mL) was added slowly to quench the reaction. Solvent was removed under reduced pressure. Ethyl acetate (~200 mL) and water (~100 mL) was added to the mixture and the aqueous phase was separated. The organic phase was further washed with brine (~50 mL×3), and dried by $Na_2SO_4$ and concentrated. The concentrated mixture was applied to 1×1 inch silica pad and eluted with diethyl ether. After the solvent was removed under vacuum, the white crystals (2r) (0.58 g, 44%) were obtained after re-crystallization from ether/hexane. Melting point: 163.7-165.8° C.; $^1$H NMR (400 MHz, $CD_2Cl_2$) δ 1.05-1.08 (m, 18H), 2.33 (s, 3H), 2.53 (s, 6H), 6.98 (s, 2H), 7.39-7.47 (m, 2H), 7.83 (d, J=7.6 Hz, 1H), 8.25 (d, J=8.4 Hz, 1H); $^{13}$C NMR (100 MHz, $CD_2Cl_2$) δ 20.7, 22.8, 22.9, 29.6, 29.8, 33.8, 34.0, 115.3, 120.5, 123.7, 125.2, 131.8, 134.5, 135.6, 141.0, 141.1, 142.5, 144.5, 155.1, 155.5 (complex unresolved C—P splitting was observed); $^{31}$P NMR (202 MHz, $CD_2Cl_2$) (11.39; IR ($cm^{-1}$) 2972.67, 2941.30, 2894.51, 2860.87, 1604.42, 1566.07, 1467.32, 1425.26, 1400.93, 1378.77, 1356.37, 1340.87, 1334.53, 1291.59, 1249.27, 1229.65, 1193.68, 1174.23, 1129.38, 1117.80, 1050.78, 1026.04, 1015.68, 932.46, 901.17, 861.23, 816.95, 765.77, 749.16, 712.24, 680.80, 670.07, 643.40, 611.40, 587.30, 560.81, 551.86, 523.13, 461.50, 439.85, 419.51; MS (EI): m/z (relative intensity) 444 ($M^+$, 0), 387 (5), 331 (6), 299 (100), 267 (77), 253 (6), 235 (15), 205 (15), 189 (10), 165 (17), 149 (28), 119 (37), 105 (10), 91 (20), 77 (8), 57 (51); HRMS: calcd. for $C_{24}H_{33}N_2O_2SPH^+$: 445.2079, found 445.2085.

EXAMPLE 25

Synthesis of 2-(di-1-adamantylphosphino)-N,N-diisopropyl-5,6-dimethyl-1H-benzo[d]imidazole-1-carboxamide (2s)

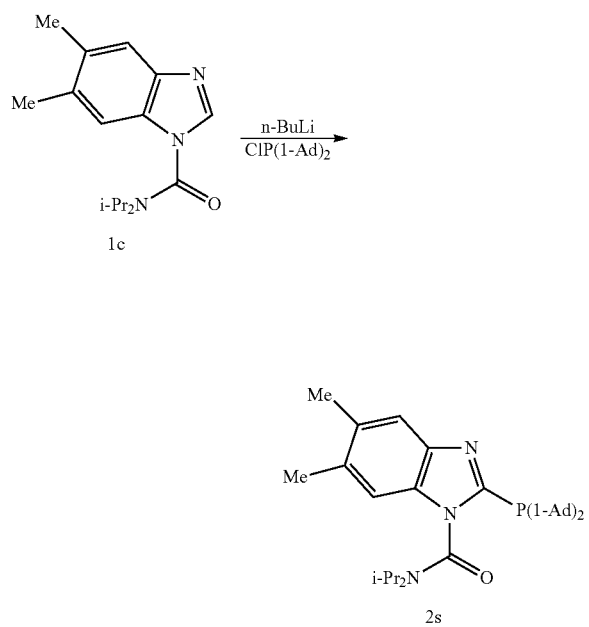

N,N-diisopropyl-5,6-dimethyl-1H-benzo[d]imidazole-1-carboxamide (1c) (0.735 g, 2.7 mmol) was dissolved in freshly distilled THF (2 mL) and toluene (30 mL) at room temperature under nitrogen atmosphere. The solution was cooled to −98° C. in methanol/liquid $N_2$ bath. Titrated n-BuLi (3.15 mmol) was added dropwise by syringe. The reaction mixture was further stirred for 10 min at −98° C. and chlorodi-1-adamantylphosphine (1.11 g, in THF/toluene, 5 mL/5 mL) was then added dropwise by syringe. The reaction was allowed to reach room temperature and stirred for overnight. MeOH (~10 mL) was added slowly to quench the reaction. Solvent was removed under reduced pressure. The white powder (2s) (0.29 g, 19%) were obtained after running column chromatography by E.A./hexane (1:9) system. $^1$H NMR (400 MHz, $CD_2Cl_2$) δ 0.93-2.42 (m, 48H), 3.65 (s, 2H), 7.13 (s, 1H), 7.61 (s, 1H); $^{13}$C NMR (100 MHz, $CD_2Cl_2$) δ 19.9, 20.2, 21.1, 21.5, 28.9, 29.0, 36.8, 38.2, 41.3, 110.3, 119.8, 131.5, 132.4, 132.8, 142.7, 150.0, 150.1, 150.4 (complex unresolved C—P splitting was observed); $^{31}$P NMR (202 MHz, $CD_2Cl_2$) δ 12.94; HRMS: calcd. for $C_{36}H_{52}N_3OPH^+$: 574.3926, found 574.3933.

EXAMPLE 26

One-pot, Two-step Synthesis of 2-(dicyclohexylphosphino)-N,N-diethyl-1H-benzo[d]imidazole-1-carboxamide (2t)

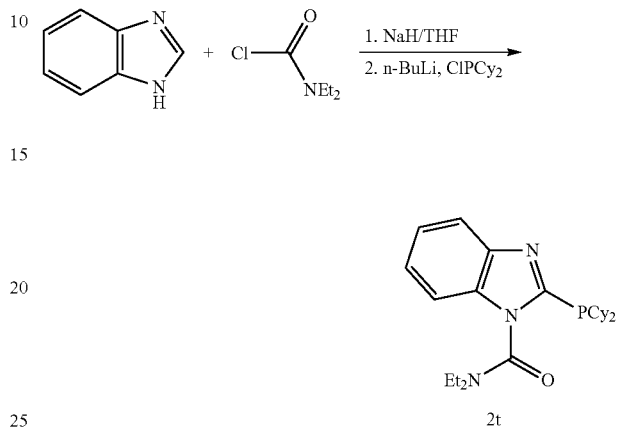

Benzimidazole (0.59 g, 5.0 mmol) was dissolved in anhydrous THF (20 mL) and added dropwise to the THF (10 mL) solution containing 1.1 equiv of NaH (60% in mineral oil, 0.22 g, 5.5 mmol) at 0° C. (Note: NaH was pre-washed with dry hexane under nitrogen). The mixture was stirred for 20 min at room temperature. Then, 1.1 equiv of N,N-diisopropylcarbamoylchloride (0.90 g, 5.5 mmol) was added directly to the reaction and the mixture was refluxed for 30 min. After the completion of the reaction as confirmed by GC-MS analysis, solvent was removed under reduced pressure. THF (1 mL) and toluene (20 mL) were added. The solution was cooled to −78° C. in acetone/liquid $N_2$ bath. Titrated n-BuLi (5.5 mmol) was added dropwise by syringe. The reaction mixture was further stirred for 10 min at −78° C. and chlorodicyclohexylphosphine (1.35 mL, 6.0 mmol) was then added dropwise by syringe. The reaction was allowed to reach room temperature and stirred for overnight. MeOH (~10 mL) was added slowly to quench the reaction. Solvent was removed under reduced pressure. The white powder (2t) (0.65 g, 30%) were obtained after running column chromatography by E.A./hexane (1:9) system. $^1$H NMR (400 MHz, $CD_2Cl_2$) δ 1.08-3.65 (m, 33H), 7.31-7.37 (m, 3H), 7.79 (t, J=8.0 Hz, 1H); $^{13}$C NMR (100 MHz, $CD_2Cl_2$) δ 26.3, 27.1, 29.9, 110.3, 119.8, 122.7, 123.7, 134.0, 143.9, 151.2, 153.7, 153.9 (complex unresolved C—P splitting was observed); $^{31}$P NMR (202 MHz, $CD_2Cl_2$) δ −14.70; HRMS: calcd. for $C_{24}H_{36}N_3OPH^+$: 414.2674, found 414.2693.

Summary of the Ligands from Examples 1-26:

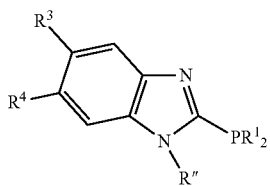

2a, R' = H, R" = C(O)Ni-Pr$_2$, R = Cy, 73%
2b, R' = H, R" = C(O)Ni-Pr$_2$, R = t-Bu, 65%
2c, R' = H, R" = C(O)Ni-Pr$_2$, R = i-Pr, 67%
2d, R' = H, R" = C(O)Ni-Pr$_2$, R = Ph, 58%
2e, R' = H, R" = C(O)Ni-Pr$_2$, R = Et, 52%
2f, R' = H, R" = Me, R = Cy, 60%
2g, R' = H, R" = Me, R = t-Bu, 37%
2h, R' = H, R" = Me, R = C$_5$H$_9$, 65%
2i, R' = Me, R" = C(O)Ni-Pr$_2$, R = Cy, 77%
2j, R' = Me, R" = C(O)Ni-Pr$_2$, R = t-Bu, 48%
2k, R' = Me, R" = C(O)Ni-Pr$_2$, R = i-Pr, 57%
2l, R' = Me, R" = C(O)Ni-Pr$_2$, R = Ph, 42%
2m, R' = Me, R" = C(O)Ni-Pr$_2$, R = o-Tol, 77%
2n, R' = H, R" = SO$_2$-2,4,6-i-Pr$_2$, R = C$_5$H$_9$, 62%
2o, R' = H, R" = SO$_2$-2,4,6-i-Pr$_3$C$_6$H$_2$, R = Cy, 77%
2p, R' = H, R" = SO$_2$-2,4,6-i-Pr$_3$C$_6$H$_2$, R = t-Bu, 29%
2q, R' = H, R" = SO$_2$-2,4,6-Me$_3$C$_6$H$_2$, R = Cy, 60%
2r, R' = H, R" = SO$_2$-2,4,6-Me$_3$C$_6$H$_2$, R = t-Bu, 44%
2s, R' = Me, R" = C(O)Ni-Pr$_2$, R = 1-Ad, 19%
2t, R' = H, R" = C(O)NEt$_2$, R = Cy, 30%

EXAMPLE 27

Catalytic Suzuki-Miyaura Cross-coupling Reaction of Aryl Chlorides

A stock solution of Pd(OAc)$_2$ (2.3 mg) with ligand in freshly distilled 10 mL THF (0.1 mol % Pd per 1 mL stock solution) was initially prepared with continuously stirring at room temperature. Arylboronic acid (1.5 mmol), K$_3$PO$_4$.H$_2$O (3.0 mmol) and magnetic stirrer bar (3 mm×8 mm) were charged to an array of Schlenk tubes. Each tube was carefully evacuated and backfilled with nitrogen (3 cycles). Aryl chloride (1.0 mmol) was then added to the Schlenk tubes. The stock solution was further diluted to give different concentrations. The diluted solutions were then transferred to Schlenk tubes via syringes. Further solvent was added (final volume 3 mL). This batch of Schlenk tube was resealed and magnetically stirred in a preheated oil bath. After the completion of reaction as judged by GC or TLC analysis, the reactions were allowed to reach room temperature. Water (~3 mL) and ethyl acetate (~10 mL×3) were added. The organic layers were combined and concentrated. The crude products were purified by column chromatography on silica gel (230-400 mesh). Alternatively, ethyl acetate (~10 mL), dodecane (227 µL, internal standard) water (~5 mL) were added. The organic layer was subjected to GC analysis. The GC yield was calibrated by authentic sample/dodecane calibration curve.

TABLE 1

Investigation on the effectiveness of the ligands 2a-2r in Suzuki-Miyaura cross-coupling reaction of 2-chlorotoluene with phenylboronic acid[a]

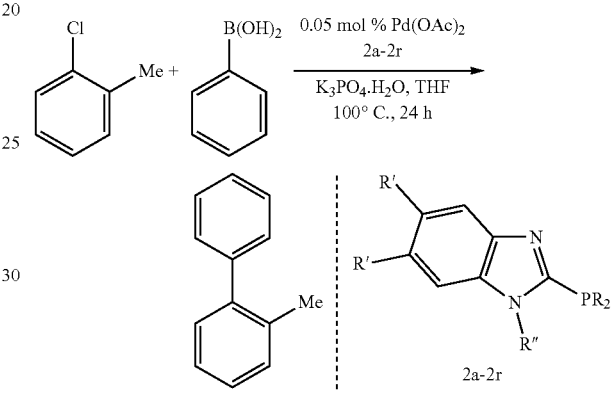

| Entry | Ligand | % Yield |
|---|---|---|
| 1 | 2a (R' = H, R" = C(O)Ni-Pr$_2$, R = Cy) | 43 |
| 2 | 2b (R' = H, R" = C(O)Ni-Pr$_2$, R = t-Bu) | 8 |
| 3 | 2c (R' = H, R" = C(O)Ni-Pr$_2$, R = i-Pr) | 18 |
| 4 | 2d (R' = H, R" = C(O)Ni-Pr$_2$, R = Ph) | 0 |
| 5 | 2e (R' = H, R" = C(O)Ni-Pr$_2$, R = Et) | 0 |
| 6 | 2f (R' = H, R" = Me, R = Cy) | 18 |
| 7 | 2g (R' = H, R" = Me, R = t-Bu) | 0 |
| 8 | 2h (R' = H, R" = Me, R = C$_5$H$_9$) | 9 |
| 9 | 2i (R' = Me, R" = C(O)Ni-Pr$_2$, R = Cy) | 57 |
| 10 | 2j (R' = Me, R" = C(O)Ni-Pr$_2$, R = t-Bu) | 13 |
| 11 | 2k (R' = Me, R" = C(O)Ni-Pr$_2$, R = i-Pr) | 23 |
| 12 | 2l (R' = Me, R" = C(O)Ni-Pr$_2$, R = Ph) | 0 |
| 13 | 2m (R' = Me, R" = C(O)Ni-Pr$_2$, R = o-Tolyl) | 0 |
| 14 | 2n (R' = Me, R" = C(O)Ni-Pr$_2$, R = C$_5$H$_9$) | 38 |
| 15 | 2o (R' = H, R" = SO$_2$-2,4,6-i-Pr$_3$C$_6$H$_2$, R = Cy) | 3 |
| 16 | 2p (R' = H, R" = SO$_2$-2,4,6-i-Pr$_3$C$_6$H$_2$, R = t-Bu) | 0 |
| 17 | 2q (R' = H, R" = SO$_2$-2,4,6-i-Me$_3$C$_6$H$_2$, R = Cy) | 3 |
| 18 | 2r (R' = H, R" = SO$_2$-2,4,6-i-Me$_3$C$_6$H$_2$, R = t-Bu) | 0 |

[a]Reaction conditions: ArCl (1.0 mmole), PhB(OH)$_2$ (1.5 mmole), K$_3$PO$_4$·H$_2$O (3.0 mmole), Pd(OAc)$_2$/L = 1:2, and THF (3 mL) were stirred for 24 h at 100° C. under nitrogen.
[b]Calibrated GC yields were reported using dodecane as the internal standard.

TABLE 2

Optimization of the reaction conditions using ligand 2i in Suzuki-Miyaura cross-coupling reaction of 2-chlorotoluene with phenylboronic acid[a]

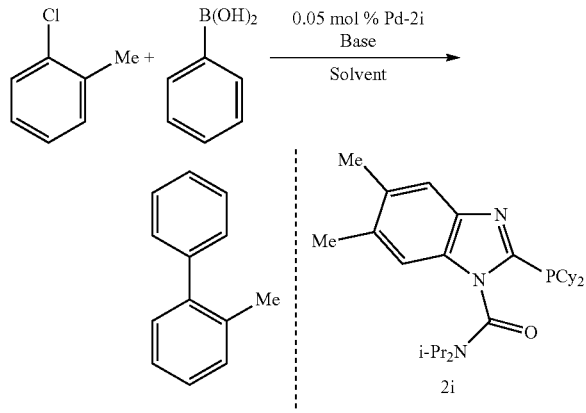

| Entry | Pd source | Pd:L | Base | Solvent | Temp. °C. | % Yield |
|---|---|---|---|---|---|---|
| 1 | Pd$_2$(dba)$_3$ | 1:2 | K$_3$PO$_4$.H$_2$O | THF | 100 | 44 |
| 2 | Pd(OAc)$_2$ | 1:2 | K$_3$PO$_4$.H$_2$O | THF | 100 | 57 |
| 3 | Pd(dba)$_2$ | 1:2 | K$_3$PO$_4$.H$_2$O | THF | 100 | 31 |
| 4 | PdCl$_2$ | 1:2 | K$_3$PO$_4$.H$_2$O | THF | 100 | 0 |
| 5 | Pd(OAc)$_2$ | 1:1 | K$_3$PO$_4$.H$_2$O | THF | 100 | 14 |
| 6 | Pd(OAc)$_2$ | 1:2.5 | K$_3$PO$_4$.H$_2$O | THF | 100 | 67 |
| 7 | Pd(OAc)$_2$ | 1:3 | K$_3$PO$_4$.H$_2$O | THF | 100 | 75 |
| 8 | Pd(OAc)$_2$ | 1:4 | K$_3$PO$_4$.H$_2$O | THF | 100 | 34 |
| 9 | Pd(OAc)$_2$ | 1:5 | K$_3$PO$_4$.H$_2$O | THF | 100 | 32 |
| 10 | Pd(OAc)$_2$ | 1:10 | K$_3$PO$_4$.H$_2$O | THF | 100 | 11 |
| 11 | Pd(OAc)$_2$ | 1:3 | K$_3$PO$_4$ | THF | 100 | 55 |
| 12 | Pd(OAc)$_2$ | 1:3 | K$_2$CO$_3$ | THF | 100 | 62 |
| 13 | Pd(OAc)$_2$ | 1:3 | Na$_2$CO$_3$ | THF | 100 | 28 |
| 14 | Pd(OAc)$_2$ | 1:3 | Cs$_2$CO$_3$ | THF | 100 | 4 |
| 15 | Pd(OAc)$_2$ | 1:3 | CsF | THF | 100 | 2 |
| 16 | Pd(OAc)$_2$ | 1:3 | NaO(t-Bu) | THF | 100 | 0 |
| 17 | Pd(OAc)$_2$ | 1:3 | K$_3$PO$_4$.H$_2$O | Dioxane | 100 | 35 |
| 18 | Pd(OAc)$_2$ | 1:3 | K$_3$PO$_4$.H$_2$O | Toluene | 100 | 17 |
| 19 | Pd(OAc)$_2$ | 1:3 | K$_3$PO$_4$.H$_2$O | t-Butanol | 100 | 13 |
| 20 | Pd(OAc)$_2$ | 1:3 | K$_3$PO$_4$.H$_2$O | THF | r.t. | 0 |
| 21 | Pd(OAc)$_2$ | 1:3 | K$_3$PO$_4$.H$_2$O | THF | 90 | 28 |
| 22 | Pd(OAc)$_2$ | 1:3 | K$_3$PO$_4$.H$_2$O | THF | 110 | 93 |

[a]Reaction conditions: ArCl (1.0 mmole), PhB(OH)$_2$ (1.5 mmole), base (3.0 mmole), and solvent (3 mL) were stirred for 24 h under nitrogen.
[b]Calibrated GC yields were reported using dodecane as the internal standard.

EXAMPLE 28

Catalytic Buchwald-Hartwig Amination Reaction of Aryl Chlorides

Pd(OAc)$_2$ (2.3 mg, 0.010 mmol) and ligand (Pd:L=1:5) were loaded into a Schlenk tube equipped with a magnetic stirrer bar (3 mm×8 mm). The tube was evacuated and flushed with nitrogen for several times. Precomplexation was applied by adding freshly distilled toluene (1 mL) and stirred for 5 min. Aryl chloride (1.0 mmol), amine (1.5 mmol), K$_2$CO$_3$ (2.5 mmol) were loaded to an array of Schlenk tubes. Further solvents were added (final volume 3 mL). This batch of Schlenk tube was resealed and magnetically stirred in a preheated 110° C. oil bath. After the completion of reaction as judged by GC or TLC analysis, the reactions were allowed to reach room temperature. Water (~3 mL) and ethyl acetate (~10 mL×3) were added. The organic layers were combined and concentrated. The crude products were purified by column chromatography on silica gel (230-400 mesh). Alternatively, ethyl acetate (~10 mL), dodecane (227 µL, internal standard) water (~5 mL) were added. The organic layer was subjected to GC analysis. The GC yield was calibrated by authentic sample/dodecane calibration curve.

TABLE 3

Investigation on the effectiveness of the ligands in Buchwald-Hartwig amination of 4-chlorotoluene with N-methylaniline[a]

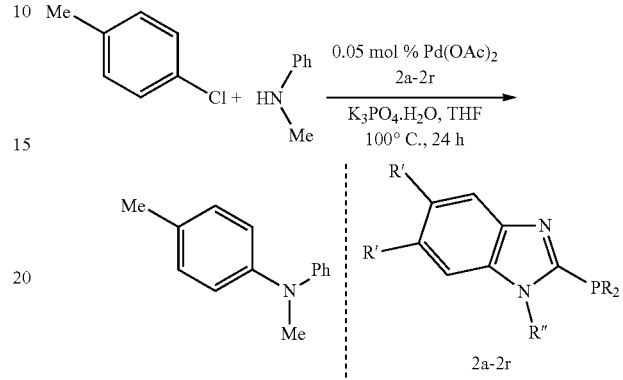

| Entry | Ligand | % Yield |
|---|---|---|
| 1 | 2a (R' = H, R" = C(O)Ni-Pr$_2$, R = Cy) | 1 |
| 2 | 2b (R' = H, R" = C(O)Ni-Pr$_2$, R = t-Bu) | 57 |
| 3 | 2c (R' = H, R" = C(O)Ni-Pr$_2$, R = i-Pr) | 1 |
| 4 | 2d (R' = H, R" = C(O)Ni-Pr$_2$, R = Ph) | 0 |
| 5 | 2f (R' = H, R" = Me, R = Cy) | 0 |
| 6 | 2g (R' = H, R" = Me, R = t-Bu) | 5 |
| 7 | 2i (R' = Me, R" = C(O)Ni-Pr$_2$, R = Cy) | 6 |
| 8 | 2j (R' = Me, R" = C(O)Ni-Pr$_2$, R = t-Bu) | 96 |
| 9 | 2k (R' = Me, R" = C(O)Ni-Pr$_2$, R = i-Pr) | 3 |
| 10 | 2l (R' = Me, R" = C(O)Ni-Pr$_2$, R = Ph) | 0 |
| 11 | 2m (R' = Me, R" = C(O)Ni-Pr$_2$, R = o-Tolyl) | 0 |
| 12 | 2o (R' = H, R" = SO$_2$-2,4,6-i-Pr$_3$C$_6$H$_2$, R = Cy) | 0 |
| 13 | 2p (R' = H, R" = SO$_2$-2,4,6-i-Pr$_3$C$_6$H$_2$, R = t-Bu) | 2 |
| 14 | 2q (R' = H, R" = SO$_2$-2,4,6-i-Me$_3$C$_6$H$_2$, R = Cy) | 0 |
| 15 | 2r (R' = H, R" = SO$_2$-2,4,6-i-Me$_3$C$_6$H$_2$, R = t-Bu) | 3 |

[a]Reaction conditions: 4-Chlorotoluene (1.0 mmole), N-methylaniline (1.5 mmole), K$_2$CO$_3$(2.5 mmole), Pd(OAc)$_2$/L = 1:4, PhB(OH)$_2$ (0.02 mmole) and toluene (3 mL) were stirred for 24 h at 110° C. under nitrogen. Calibrated GC yields were reported using dodecane as the internal standard.

TABLE 4

Optimization of the reaction conditions using ligand 2j in Buchwald-Hartwig amination of 4-chlorotoluene with N-methylaniline[a]

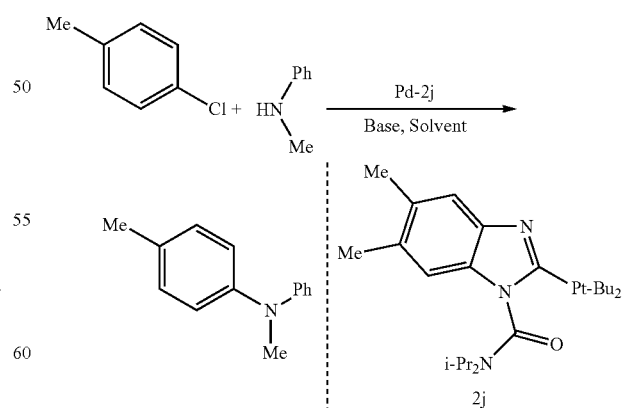

| Entry | Pd source | Pd:L | mol % Pd | Base | Solvent | % Yield |
|---|---|---|---|---|---|---|
| 1 | Pd$_2$(dba)$_3$ | 1:4 | 0.5 | K$_2$CO$_3$ | Toluene | 74 |
| 2 | Pd(OAc)$_2$ | 1:4 | 0.5 | K$_2$CO$_3$ | Toluene | 80 |

TABLE 4-continued

Optimization of the reaction conditions using ligand 2j in Buchwald-Hartwig amination of 4-chlorotoluene with N-methylaniline[a]

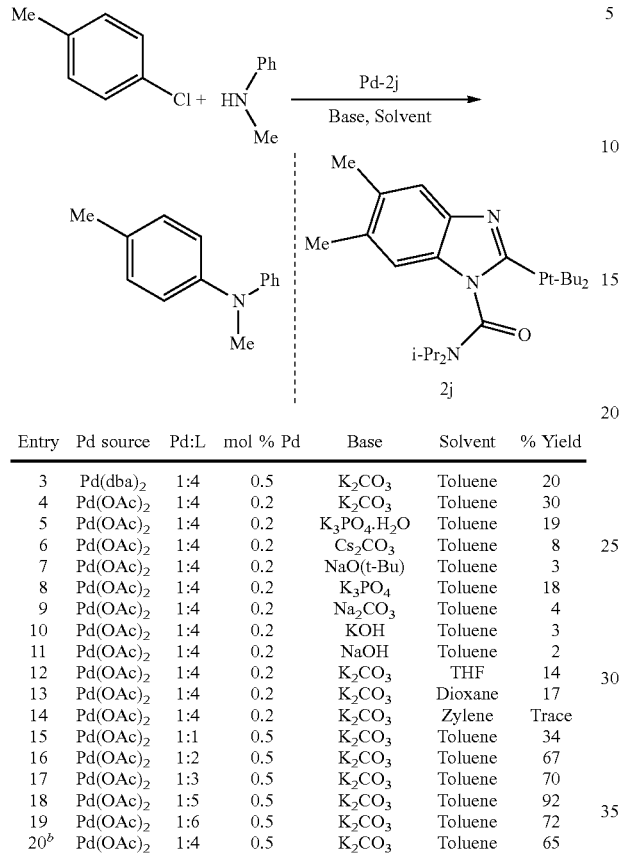

| Entry | Pd source | Pd:L | mol % Pd | Base | Solvent | % Yield |
|---|---|---|---|---|---|---|
| 3 | Pd(dba)$_2$ | 1:4 | 0.5 | K$_2$CO$_3$ | Toluene | 20 |
| 4 | Pd(OAc)$_2$ | 1:4 | 0.2 | K$_2$CO$_3$ | Toluene | 30 |
| 5 | Pd(OAc)$_2$ | 1:4 | 0.2 | K$_3$PO$_4$.H$_2$O | Toluene | 19 |
| 6 | Pd(OAc)$_2$ | 1:4 | 0.2 | Cs$_2$CO$_3$ | Toluene | 8 |
| 7 | Pd(OAc)$_2$ | 1:4 | 0.2 | NaO(t-Bu) | Toluene | 3 |
| 8 | Pd(OAc)$_2$ | 1:4 | 0.2 | K$_3$PO$_4$ | Toluene | 18 |
| 9 | Pd(OAc)$_2$ | 1:4 | 0.2 | Na$_2$CO$_3$ | Toluene | 4 |
| 10 | Pd(OAc)$_2$ | 1:4 | 0.2 | KOH | Toluene | 3 |
| 11 | Pd(OAc)$_2$ | 1:4 | 0.2 | NaOH | Toluene | 2 |
| 12 | Pd(OAc)$_2$ | 1:4 | 0.2 | K$_2$CO$_3$ | THF | 14 |
| 13 | Pd(OAc)$_2$ | 1:4 | 0.2 | K$_2$CO$_3$ | Dioxane | 17 |
| 14 | Pd(OAc)$_2$ | 1:4 | 0.2 | K$_2$CO$_3$ | Zylene | Trace |
| 15 | Pd(OAc)$_2$ | 1:1 | 0.5 | K$_2$CO$_3$ | Toluene | 34 |
| 16 | Pd(OAc)$_2$ | 1:2 | 0.5 | K$_2$CO$_3$ | Toluene | 67 |
| 17 | Pd(OAc)$_2$ | 1:3 | 0.5 | K$_2$CO$_3$ | Toluene | 70 |
| 18 | Pd(OAc)$_2$ | 1:5 | 0.5 | K$_2$CO$_3$ | Toluene | 92 |
| 19 | Pd(OAc)$_2$ | 1:6 | 0.5 | K$_2$CO$_3$ | Toluene | 72 |
| 20[b] | Pd(OAc)$_2$ | 1:4 | 0.5 | K$_2$CO$_3$ | Toluene | 65 |

[a]Reaction conditions: 4-Chlorotoluene (1.0 mmole), N-methylaniline (1.5 mmole), base (2.5 mmole), PhB(OH)$_2$ (0.02 mmole) and solvent (3 mL) were stirred for 24 h at 110° C. under nitrogen. Calibrated GC yields were reported using dodecane as the internal standard.
[b]At 100° C.

What is claimed is:

1. A phosphine ligand having the structure of formula (2):

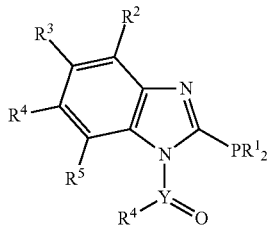

wherein Y represents C or SO;
each of the two R$^1$ independently represents alkyl; cycloalkyl; aryl; or heteroaryl, wherein the number of hetero atoms, selected from the group of N, O and S, may be 1 or 2;
and each of R$^2$-R$^6$ independently represents hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carbonyl, silyl, thioalkyl, alkylsulfonyl, arylsulfonyl, selenoalkyl, heteroalkyl, nitrile, guanidine, amidine, acetal, ketal, amine oxide, aryl, heteroaryl, azide, aziridine, epoxide, imide, oxime, sulfonamide, thioamide, thiocarbamate, urea, or thiourea.

2. The phosphine ligand of claim 1, wherein the cycloalkyl is monocyclic, bi- or tri-cyclic cycloalkyl; aryl is phenyl, naphthyl, or fluorenyl; and carbonyl is amide, carboxyl, carboxamide, anhydride, ketone, aldehyde, ester, carbamate or hydroxamic acid.

3. A phosphine ligand having the structure of formula (2):

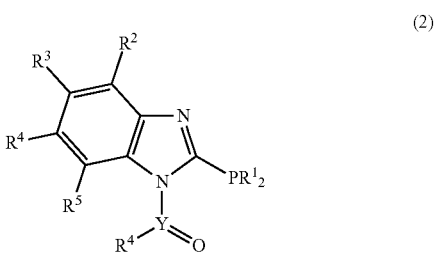

wherein Y represents C or SO;
each of the two R$^1$ independently represents alkyl; cycloalkyl; aryl; or heteroaryl, wherein the number of hetero atoms, selected from the group of N, O and S, may be 1 or 2; or the two R$^1$ are linked to one another;
and each of R$^2$-R$^6$ independently represents hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carbonyl, silyl, thioalkyl, alkylsulfonyl, arylsulfonyl, selenoalkyl, heteroalkyl, nitrile, guanidine, amidine, acetal, ketal, amine oxide, aryl, heteroaryl, azide, aziridine, epoxide, imide, oxime, sulfonamide, thioamide, thiocarbamate, urea, or thiourea.

4. The phosphine ligand of claim 3, wherein the cycloalkyl is monocyclic, bi- or tri-cyclic cycloalkyl; aryl is phenyl, naphthyl, or fluorenyl; and carbonyl is amide, carboxyl, carboxamide, anhydride, ketone, aldehyde, ester, carbamate or hydroxamic acid.

5. A phosphine ligand having the structure of formula (2):

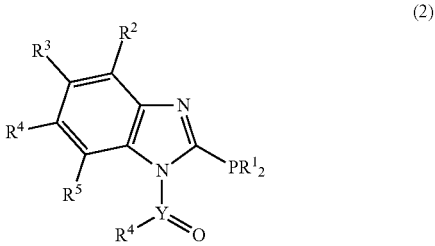

wherein Y represents C or SO;
each of the two R$^1$ independently represents alkyl; cycloalkyl; aryl; or heteroaryl, wherein the number of hetero atoms, selected from the group of N, O and S, may be 1 or 2;
and each of R$^2$-R$^6$ independently represents hydrogen, halogen, alkyl, alkenyl, alkynyl, hydroxyl, alkoxyl, silyloxy, amino, nitro, sulfhydryl, alkylthio, imine, phosphoryl, phosphonate, phosphine, carbonyl, silyl, thioalkyl, alkylsulfonyl, arylsulfonyl, selenoalkyl, heteroalkyl, nitrile, guanidine, amidine, acetal, ketal, amine oxide, aryl, heteroaryl, azide, aziridine, epoxide, imide, oxime, sulfonamide, thioamide, thiocarbamate, urea, or thiourea; or two or more of $R^2$, $R^3$, $R^4$, $R^5$ and $R^6$ of formula (2), when adjacent to one another, are linked to one another to form a condensed ring system.

6. The phosphine ligand of claim 5, wherein the cycloalkyl is monocyclic, bi- or tri-cyclic cycloalkyl; aryl is phenyl, naphthyl, or fluorenyl; and carbonyl is amide, carboxyl, carboxamide, anhydride, ketone, aldehyde, ester, carbamate or hydroxamic acid.

7. The phosphine ligand of claim 1, selected from the group consisting of:
- 2-(dicyclohexylphosphino)-N,N-diisopropyl-1H-benzo[d]imidazole-1-carboxamide (2a),
- 2-(di-tert-butylphosphino)-N,N-diisopropyl-1H-benzo[d]imidazole-1-carboxamide (2b),
- 2-(diisopropylphosphino)-N,N-diisopropyl-1H-benzo[d]imidazole-1-carboxamide (2c),
- 2-(diphenylphosphino)-N,N-diisopropyl-1H-benzo[d]imidazole-1-carboxamide (2d),
- 2-(diethylphosphino)-N,N-diisopropyl-1H-benzo[d]imidazole-1-carboxamide (2e),
- 2-(dicyclohexylphosphino)-N,N-diisopropyl-5,6-dimethyl-1H-benzo[d]imidazole-1-carboxamide (2i),
- 2-(di-tert-butylphosphino)-N,N-diisopropyl-5,6-dimethyl-1H-benzo[d]imidazole-1-carboxamide (2j),
- 2-(diisopropylphosphino)-N,N-diisopropyl-5,6-dimethyl-1H-benzo[d]imidazole-1-carboxamide (2k),
- 2-(diphenylphosphino)-N,N-diisopropyl-5,6-dimethyl-1H-benzo[d]imidazole-1-carboxamide (2l),
- 2-(di-o-tolylphosphino)-N,N-diisopropyl-5,6-dimethyl-1H-benzo[d]imidazole-1-carboxamide (2m),
- 2-(dicyclopentylphosphino)-N,N-diisopropyl-5,6-dimethyl-1H-benzo[d]imidazole-1-carboxamide (2n),
- 2-(dicyclohexylphosphino)-1-(2,4,6-triisopropylphenylsulfonyl)-1H-benzo[d]imidazole (2o),
- 2-(di-tert-butylphosphino)-1-(2,4,6-triisopropylphenylsulfonyl)-1H-benzo[d]imidazole (2p),
- 2-(dicyclohexylphosphino)-1-(mesitylsulfonyl)-1H-benzo[d]imidazole (2q),
- 2-(di-tert-butylphosphino)-1-(mesitylsulfonyl)-1H-benzo[d]imidazole (2r),
- 2-(di-1-adamantylphosphino)-N,N-diisopropyl-5,6-dimethyl-1H-benzo[d]imidazole-1-carboxamide (2s), and
- 2-(dicyclohexylphosphino)-N,N-diethyl-1H-benzo[d]imidazole-1-carboxamide (2t).

8. A method of synthesizing the phosphine ligand of claim 1, comprising steps of:
a) condensing an appropriate benzimidazole with an acyl chloride or sulfonyl chloride; and
b) coupling the condensation product from step a) with an appropriate chlorophosphine to form said phosphine ligand.

9. The method of claim 8, wherein step a) is carried out with a base in an organic solvent.

10. The method of claim 9, wherein said base is selected from the group consisting of sodium hydride, sodium hydroxide, potassium hydride, potassium hydroxide and calcium hydride.

11. The method of claim 9, wherein said solvent is selected from the group consisting of tetrahydrofuran, toluene, and a combination thereof.

12. The method of claim 8, wherein step b) is carried out with a base.

13. The method of claim 12, wherein said base is selected from the group consisting of n-butyllithium and lithium diisopropylamide.

14. The method of claim 8, wherein said method is a one-pot, two-step process.

15. The method of claim 8, wherein said phosphine ligand is selected from the group consisting of:
- 2-(dicyclohexylphosphino)-N,N-diisopropyl-1H-benzo[d]imidazole-1-carboxamide (2a),
- 2-(di-tert-butylphosphino)-N,N-diisopropyl-1H-benzo[d]imidazole-1-carboxamide (2b),
- 2-(diisopropylphosphino)-N,N-diisopropyl-1H-benzo[d]imidazole-1-carboxamide (2c),
- 2-(diphenylphosphino)-N,N-diisopropyl-1H-benzo[d]imidazole-1-carboxamide (2d),
- 2-(diethylphosphino)-N,N-diisopropyl-1H-benzo[d]imidazole-1-carboxamide (2e),
- 2-(dicyclohexylphosphino)-N,N-diisopropyl-5,6-dimethyl-1H-benzo[d]imidazole-1-carboxamide (2i),
- 2-(di-tert-butylphosphino)-N,N-diisopropyl-5,6-dimethyl-1H-benzo[d]imidazole-1-carboxamide (2j),
- 2-(diisopropylphosphino)-N,N-diisopropyl-5,6-dimethyl-1H-benzo[d]imidazole-1-carboxamide (2k),
- 2-(diphenylphosphino)-N,N-diisopropyl-5,6-dimethyl-1H-benzo[d]imidazole-1-carboxamide (2l),
- 2-(di-o-tolylphosphino)-N,N-diisopropyl-5,6-dimethyl-1H-benzo[d]imidazole-1-carboxamide (2m),
- 2-(dicyclopentylphosphino)-N,N-diisopropyl-5,6-dimethyl-1H-benzo[d]imidazole-1-carboxamide (2n),
- 2-(dicyclohexylphosphino)-1-(2,4,6-triisopropylphenylsulfonyl)-1H-benzo[d]imidazole (2o),
- 2-(di-tert-butylphosphino)-1-(2,4,6-triisopropylphenylsulfonyl)-1H-benzo[d]imidazole (2p),
- 2-(dicyclohexylphosphino)-1-(mesitylsulfonyl)-1H-benzo[d]imidazole (2q),
- 2-(di-tert-butylphosphino)-1-(mesitylsulfonyl)-1H-benzo[d]imidazole (2r),
- 2-(di-1-adamantylphosphino)-N,N-diisopropyl-5,6-dimethyl-1H-benzo[d]imidazole-1-carboxamide (2s), and
- 2-(dicyclohexylphosphino)-N,N-diethyl-1H-benzo[d]imidazole-1-carboxamide (2t).

16. The method of claim 8, further comprising a step of purifying said phosphine ligand by recrystallization.

17. A method of catalyzing a reaction, comprising a step of adding the phosphine ligand of claim 1 to said reaction.

18. The method of claim 17, wherein said reaction is Suzuki-Mayaura cross-coupling reaction.

19. The method of claim 17, wherein said reaction is Buchwald-Hartwig amination reaction.

* * * * *